United States Patent [19]
Graff et al.

[11] Patent Number: 5,962,291
[45] Date of Patent: Oct. 5, 1999

[54] METAL DEPENDENT CATALYTIC ANTIBODIES AND METHOD FOR PRODUCING THE SAME

[75] Inventors: Darla A. Graff, Denver; Marvin H. Caruthers, Boulder, both of Colo.; Jeffrey W. Jacobs, San Mateo, Calif.

[73] Assignee: The Regents of the University of Colorado, Boulder, Colo.

[21] Appl. No.: 08/949,220

[22] Filed: Oct. 10, 1997

Related U.S. Application Data

[63] Continuation of application No. 08/634,992, Apr. 19, 1996, abandoned.

[51] Int. Cl.$^6$ ............................... C12N 9/00; C12N 5/12
[52] U.S. Cl. .................... 435/188.5; 435/346; 530/388.9
[58] Field of Search ................................ 435/188.5, 346; 530/388.9

[56] References Cited

U.S. PATENT DOCUMENTS

| | | | |
|---|---|---|---|
| 4,722,892 | 2/1988 | Meares et al. | 435/7 |
| 5,503,987 | 4/1996 | Wagner et al. | 435/7.94 |

OTHER PUBLICATIONS

"At the Crossroads of Chemistry and Immunology: Catalytic Antibodies," Lerner, Benkovic and Schultz, *Science*, 252:659–667 (1991).
"Direct Selection of Antibodies that Coordinate Metals from Semisynthetic Combinatorial Libraries," Barbas, Rosenblum and Lerner, *Proc. Natl. Acad. Sci. USA*, 90:6385–6389 (1993).
"Antibody–Catalyzed Hydrolysis of Phosphate Monoesters," Scanlan, Prudent and Schultz, *J. Am. Chem. Soc.*, 113:9397–9398 (1991).
"A Highly Specific Metal–Activated Catalytic Antibody," Wade, Ashley, Jahangiri, et al., *J. Am. Chem. Soc.*, 115:4906–4907 (1993).
"Engineering Metal Coordination Sites into the Antibody Light Chain," Wade, Koh, Han, Hoekstra and Lerner, *J. Am. Chem. Soc.*, 115:4449–4456 (1993).
"Antibodies Against Metal Chelates," Reardan, Meares, Goodwin, et al., *Nature*, 316:265–268 (1985).
"Sequence–Specific Peptide Cleavage Catalyzed by an Antibody," Iverson and Lerner, *Science*, 243:1184–1188 (1989).
"Metalloselective Anti–Porphyrin Monoclonal Antibodies," Schwabacher, Weinhouse, Auditor and Lerner, *J. Am. Chem. Soc.*, 111:2344–2346 (1989).
"New Synthetic Route to Unsymmetrically Substituted Pentacoordinated Phosphorus. Hydrolytically Stable Chiral Monocyclic Oxyphosphoranes," Moriarty, Hiratake and Liu, *J. Am. Chem. Soc.*, 112:8575–8577 (1990).
"Antibody–Catalyzed Porphyrin Metallation," Cochran and Schultz, *Science*, 249:781–783 (1990).
"Synthesis of Dinucleoside and Dinucleotide Phosphorodithioates Via a Phosphotriester Approach," Yau, Ma and Caruthers, *Tetrahedron Letters*, 31(14):1953–1956 (1990).
"Phosphorodithioate DNA as a Potential Therapeutic Drug," Marshall and Caruthers, *Science*, 259:1564–1570 (1993).
Wade, W. S., et. al. (1993) J. Am. Chem. Soc. 115, 4906–4907.
Janda, K. D., et. al. (1990) J. Am. Chem. Soc. 112, 1274–1275.
Barbas, C. F., et al (1993) Proc. Natl. Acad. Sci., USA 90, 6385–6389.
Roberts, V. A., et. al. (1995) Faseb J. 9, 94–100.
Gololobov, G. V., et. al. (1993 Indian J. Of Chem. 32B, 81–84.
James, K, et. al. (1987) J. Immunol. Meth. 100, 5–40.
Abrams, P. G., et. al. (1986) Meth. Enzymol. 121, 107–119.

*Primary Examiner*—Charles L. Patterson, Jr.
*Attorney, Agent, or Firm*—Steven C. Petersen; Chrisman Bynum & Johnson

[57] ABSTRACT

The present invention relates to catalytic antibodies and a method for producing the same wherein a host is immunized using an "antigen chelate" or more specifically a stable compound capable of chelating metal ions. The immune response mounted in response to the antigen chelate produces antibodies that are capable of binding both a substrate and a metal ion, thus achieving a metal cofactor assisted reaction.

38 Claims, 7 Drawing Sheets

METAL DEPENDENT CATALYTIC ANTIBODIES AND METHOD FOR PRODUCING THE SAME

This application is a continuation of application Ser. No. 08/634,992, filed Apr. 19, 1996, now abandoned.

CONTRACTUAL ORIGIN OF THE INVENTION

This study was supported by National Institutes of Health grant GM21120 and GM25680 (to M.H.C.), and Damon Runyon-Walter Winchell Cancer Research Fund DRG-1036 (to J.W.J.), and has been assigned to the Regents of the University of Colorado.

BACKGROUND OF THE INVENTION

1. Field of the Invention

The present invention relates to catalytic antibodies, and more particularly to catalytic antibodies and a method for producing catalytic antibodies which are capable of hydrolyzing phosphoester bonds in a metal dependent manner.

2. Description of the State of Art

Chemical reactions in biological systems rarely occur in the absence of a catalyst. These catalysts, referred to as enzymes, are highly specific in the reactions they catalyze and the substrates utilized, and while they may go through temporary changes they are not consumed in the reaction. Enzymes accelerate reactions by factors of at least a million. Indeed, most reactions in biological systems do not occur at perceptible rates in the absence of enzymes. For example, it has been estimated that the phosphodiester bonds in DNA have a half-life for hydrolytic cleavage of 200 million years. In contrast, many DNases (enzymes that catalyze this reaction) can hydrolyze the phosphodiester bonds in DNA in a matter of seconds.

An enzyme, as a catalyst, cannot alter the equilibrium of a chemical reaction. This means that an enzyme accelerates the forward and reverse reaction by precisely the same factor. Consider the interconversion of A and B. Suppose that in the absence of enzyme the forward rate ($k_F$) is $10^{-3}$ sec$^{-1}$ and the reverse rate ($k_R$) is $10^{-5}$ sec$^{-1}$. The equilibrium constant K is given by the ratio of these rates.

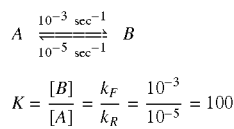

The equilibrium concentration of B is 100 times that of A, whether or not enzyme is present. However, it will take several hours to approach this equilibrium without enzyme, whereas equilibrium would be attained within a second when enzyme is present. Thus, enzymes accelerate the attainment of equilibria but do not shift their positions.

A chemical reaction, A⇌B, goes through a transition state that has a higher energy than either A or B. The rate of the forward reaction depends on the temperature and on the difference in free energy between that of A and the transition state, which is referred to as the Gibbs free energy of activation and symbolized $\Delta G^{\ddagger}$, as shown in FIG. 1a.

$$\Delta G^{\ddagger} = G_{transition\ state} - G_{substrate}$$

Enzymes accelerate reactions by decreasing $\Delta G^{\ddagger}$, the activation barrier. The combination of substrate and enzyme at a specific region of the enzyme called the active site, creates a new reaction pathway whose transition state energy is lower than it would be if the reaction were taking place in the absence of enzyme as shown in FIG. 1b.

The design and generation of efficient catalysts with any desired specificity is a "holy grail" for chemists and biochemists alike. Chemists have concentrated on the use of nature's most efficient catalysts, the enzymes, in the field of organic synthesis (see, Wong, C. H., et al., Curr. Opinion. Struc. Biol., 8:694 (1993)), "host-guest" interactions or supramolecular chemistry, and in the use of small, reactive organic molecules as models of enzymes. Likewise, biochemists have used molecular biology as well as chemical techniques to modify existing biological molecules. Recently chemistry and biochemistry have met in the development of catalytic antibodies. Here, an understanding of chemical reactivity has been combined with the diversity of the immune system to generate antibodies capable of not only binding to their antigens, but effecting chemical reactions upon them. Since the first reports of catalytic antibodies in 1986, over fifty different reactions have been shown to be antibody catalyzed (Lerner, R. A., et al., Science, 252:659 (1991)). However, no metal dependent catalytic antibodies currently exist that can hydrolyze phosphate ester bonds, and while catalysts for hydrolyzing phosphate esters have representatives in many of the fields mentioned previously, they lack the specificity to which catalytic antibodies would lend themselves.

Antibodies or immunoglobulins (Ig's) are large proteins that consist of four polypeptide chains: two identical light (L) chain polypeptides and two identical heavy (H) chain polypeptides held together by disulfide bridges and non-covalent bonds. The four chains contain defined Variable (V), Diversity (D) (heavy chain only), Joining (J) and Constant (C) regions. The DNA and amino acid sequence of the C region is relatively conserved within a given animal species while the V region sequence is antigen-dependent. Pairing of the heavy and light chain V regions creates an antigen-binding site (paratope) which recognizes a single antigenic determinant (epitope). Within each variable region are three complementarily-determining regions (CDRs) of extremely high variability which provide the basis for the diversity of the antibody molecule. The specificity of antibodies for their antigens can exceed that of enzymes for substrates. Antibodies bind antigens or haptens with association constants that range from $10^4$ to $10^{14}$ M$^{-1}$. Small antigens are typically bound in a cleft, but for larger molecules the binding site can be an extended surface that can cover 600 to 800 Å$^2$.

While the genetic mechanism whereby an antibody gene forms has been estimated to be capable of producing over $10^{11}$ different antibody molecules for an individual, the range of reactions that can be catalyzed by enzymes composed of only the 20 natural amino acids fall far short of this number. Enzymes, however, may utilize the existence of nonpeptidyl catalytic auxiliaries, referred to as cofactors, to greatly expand the range of reactions that can be catalyzed. These cofactors include metal ions, hemes, thiamine, flavins, and pyridoxal phosphate.

Metal ions have long been recognized as essential components of living systems, and strategies that would allow incorporation of metal ions into antibody combining sites should, by analogy to enzymes, expand the scope of antibody catalysis. In this case, metal ions may play a number of roles. One would be the ability to orient the substrate correctly in the active site, serving as a template by neutralizing anionic charges on the substrate. A second would be to act as a super Lewis acid, activating the substrate by withdrawing electrons from the substrate, making it more susceptible to nucleophilic attack. Another role would be to coordinate the attaching water molecule in a manner that greatly reduces its $pK_a$ and aids the delivery of a hydroxide ion nucleophile at physiological pH.

There have been some attempts at engineering metal binding antibodies. For example, Sarvetnick, N., et al., disclosed their attempt to create a metal-binding antibody which involved producing transgenic mice with a metal ion-binding light chain in the genome. The light chain has a three-histidine site with specificity for Cu(II) and Zn(II). These transgenic mice were immunized with a fluorescein conjugate. The three-histidine light chain was found in two of six hybridomas isolated. While this work is encouraging with regards to expanding the chemical potential of the immune system, there are, however, some concerns. The authors did not show that metal ions actually bound to the isolated antibodies, and furthermore, this work did not demonstrate that a metal ion and the fluorescein antigen bind simultaneously, or in a geometry that allows for a chemical reaction (Sarvetnick, N., et al., *Proceedings of the National Academy of Sciences.*, 90:4008 (1993)).

A more systematic approach involved engineering the three-histidine site into a light chain variant of the same antibody, disclosed by Wade, W. S., et al. Four sites were modified and it was shown that all mutant antibodies bound fluorescein. Based on tryptophan fluorescence quenching, two of the four sites exhibited metal affinities consistent with complexation by three ligands. The specificity of the tightest binding site was probed by mutagenesis. Here, the second highest isolated affinity site showed a metal-dependent increase in fluorescein binding, which indicates a ternary complex. Several combinations of modifications having only four amino acid changes gave affinities in a potentially useful range for antibody catalysis (Wade, W. S., et al., *J. Am. Chem. Soc.*, 115:4449 (1993)).

As an alternate approach, Pessi and coworkers have generated what they call the "minibody". This molecule was constructed by incorporating the three-histidine metal-binding site into the immunoglobulin heavy chain variable domain. The resulting molecule had a novel β-sheet scaffold and two regions corresponding to hypervariable loops. The protein was folded, compact and bound metal ions (Pessi, A., et al., *Nature*, 362:367 (1993)).

The alternative to engineering metal-binding antibodies as discussed above has focused solely on inducing antibodies to transition state analogues as haptens. For example, Lerner and coworkers were the first to use cofactor containing haptens successfully for the induction of catalytic antibodies capable of cofactor-assisted peptide bond cleavage. Antibodies were made against a covalent $[Co^{3+}N_4]$ compound that mimicked the transition state of a cofactor-assisted peptide bond cleavage. This work, however encouraging, was preliminary, as no kinetic constants were presented, and further work has not appeared (Lerner, R. A., et al., *Proceedings of the National Academy of Sciences*, 90:6385–6389 (1993)). Another example of cofactors in catalytic antibodies is an antibody-catalyzed porphyrin metallation. Ferrochelatase is an enzyme that catalyzes the insertion of $Fe^{2+}$ into protoporphyrin. N-alkylated porphyrins have a distorted macrocycle and are thought to closely resemble the transition state for the chelation of the porphyrin. Antibodies were generated against the putative transition state analogue N-methyl-mesoporphyrin IX; however, no metal ion was present in the hapten. Also, the authors reported that binding of metal ions by the antibody was not saturable, and did not contribute to catalysis in any significant way (Schultz, P. G., et al., *Science* 249:781–783 (1990)).

The most recent example of a catalytic antibody utilizing cofactors is one where the antibody was not generated to metal ions or metal ions complexes. A rationally designed hapten with structural features that could translate into induction of antibodies with a metal binding pocket was used. It was determined that one of the antibodies utilized a substrate with a pyridine moiety only when it was complexed with $Zn^{2+}$. However, no antibodies with metal ion binding sites were obtained (Lerner, R. A., et al., *J. Am. Chem. Soc.*, 115:4906–4907 (1993)).

To date, research in the field of metal dependent catalytic antibody induction is based entirely on using transition state analogues as haptens. This approach to generating catalytic antibodies however is problematic for the hydrolysis of phosphodiesters. The transition state for phosphodiester bond hydrolysis is trigonal pyramidal; that is, 5-coordinate. The classical approach to generating catalytic antibodies for phosphodiester bond hydrolysis would be to synthesize a suitably stable 5-coordinate compound for use as a hapten and screen the resulting antibodies for catalytic activity. Unfortunately, phosphorus does not form stable 5-coordinate complexes that resemble this transition state. Other elements, such as vanadium (V), with this geometry are too unstable in aqueous solutions and would be hydrolyzed before an immune response could be mounted. Currently there is no known catalytic antibody that can hydrolyze phosphodiester bonds, nor are there any known catalytic antibodies that can independently bind a metal ion that acts as a cofactor in a chemical reaction.

There is still a need, therefore, for catalytic antibodies and a method for producing catalytic antibodies that are capable of hydrolyzing phosphodiester bonds in a metal dependent manner.

SUMMARY OF THE INVENTION

Accordingly, it is an object of this invention to provide a method for the generation of cofactor-dependent catalytic antibodies.

It is an additional object of this invention to provide a method for the generation of catalytic antibodies with combining sites containing coordination spheres capable of accommodating a variety of metals.

It is still a further object of this invention to generate catalytic antibodies capable of hydrolyzing phosphodiester bonds in a metal dependent manner.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein the metal dependent catalytic antibodies of this invention and method of this invention for producing the same comprises immunizing a host with antigen chelates, wherein the antigen chelates comprise a free metal ion and a compound or its analogues that have an affinity for the free metal ions; harvesting from the host, cells producing an antibody to the antigen chelate; and finally identifying those antibodies capable of binding a substrate and a free metal ion.

BRIEF DESCRIPTION OF THE DRAWINGS

The accompanying drawings, which are incorporated in and form a part of the specifications, illustrate the preferred embodiments of the present invention, and together with the description serve to explain the principles of the invention.

In the Drawings.

DETAILED DESCRIPTION OF THE PREFERRED EMBODIMENT

In general, the catalytic antibodies and method for inducing catalytic antibodies according to this invention do not rely on the classical transition state analogue approach, but rather depend directly on eliciting antibodies to a hapten in the form of a stable derivative of a phosphodiester substrate capable of chelating metal ions. Such a hapten is not possible with normal phosphodiester bonds since their affinity for free metal ions is either low or the resulting complexes are hydrolytically unstable. Hence, the preferred embodiment of the present invention comprises a hapten having the two non-bridging oxygens of the phosphodiester bond replaced by sulfur thereby producing a phosphorodithioate analogue hapten. This phosphorodithioate hapten of the present invention is then attached to a carrier protein to produce an antigen prior to immunization.

Figure 1A:
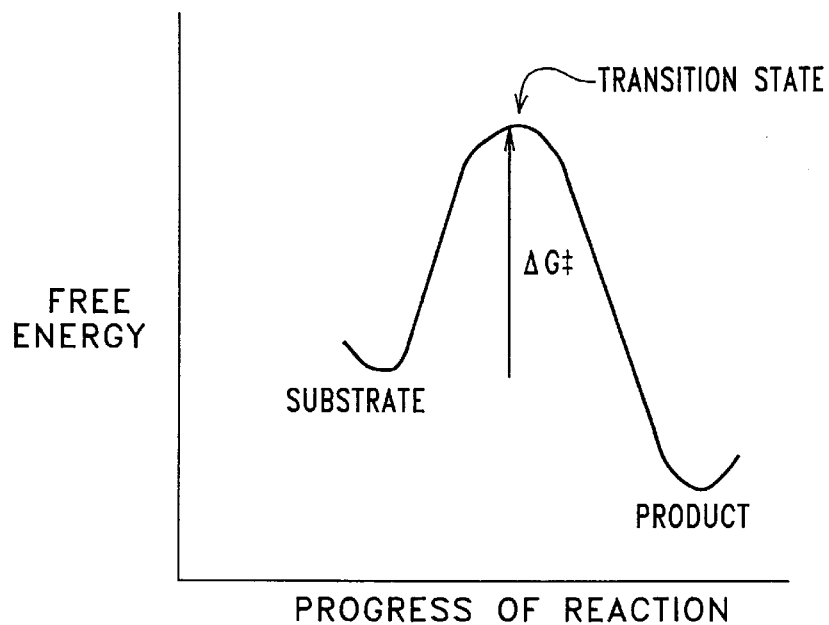
FIG. 1a is a schematic representation of the definition of $\Delta G^{\ddagger}$, the free energy of activation.
Figure 1B:
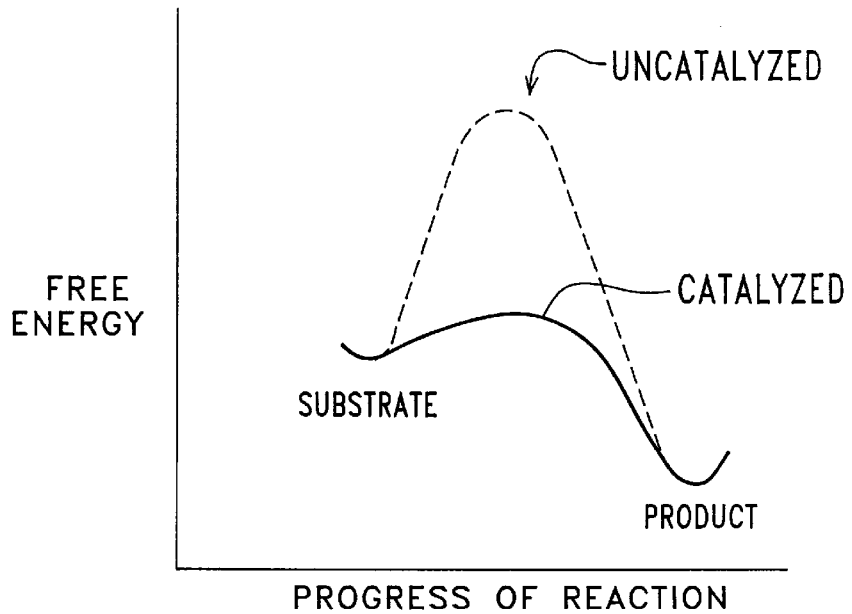
FIG. 1b is a schematic representation of how enzymes accelerate catalysis by reducing $\Delta G^{\ddagger}$.
Figure 2:
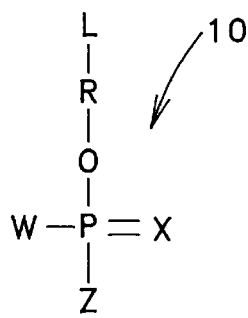
FIG. 2 is a schematic representation of the structure of a phosphodiester linkage and modified derivatives, used in the present invention to induce catalytic antibodies.

As discussed above, the process of the present invention and products produced thereby is grounded in the formation of a stable substrate metal ion chelate hapten. Hapten 10, shown in FIG. 2, is a schematic representation of the hapten having a stable phosphorous center used to induce catalytic antibodies according to the present invention wherein, L is a linker which facilitates attachment of hapten 10 to a carrier protein (not shown), P is phosphorus, O is oxygen, R is a chemical compound, and each of W, X and Z can be either a chemical compound or a chemical element; or R and Z are chemical compounds wherein the chemical compound of Z is attached to the phosphorus by oxygen and W and X are sulfur, (phosphorodithioate); or W is a sulfur and X is oxygen, (phosphorothioate); or W is methyl and X is oxygen, (methylphosphonate); or W is $NR_2$ and X is oxygen, where R is alkyl or aryl substituents, (phosphoramidate).

Figure 3:
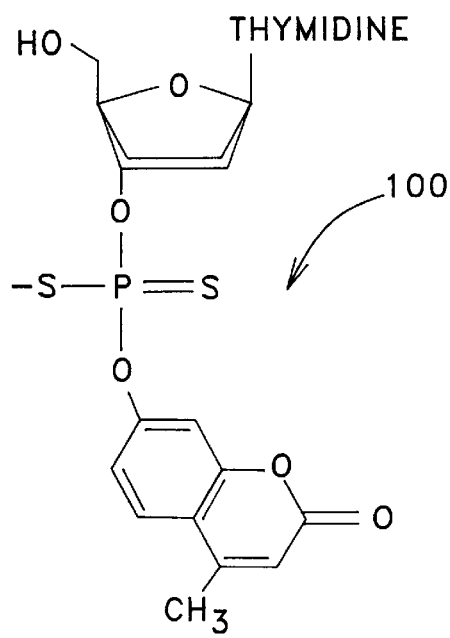
FIG. 3 is a schematic representation of the structure of a phosphorodithioate hapten of the present invention used for the induction of antibodies following chelation of metals.
Figure 4:
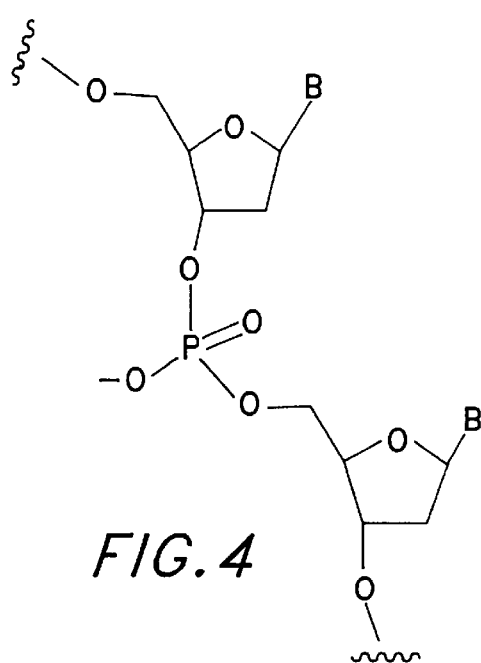
FIG. 4 is a schematic representation of the structure of a typical phosphodiester deoxyribonucleic acid (DNA) molecule.

In the discussion which follows hapten or thymidine 3'-O-(7-hydroxy-4-methyl coumarin) phosphorodithioate 100, as shown in FIG. 3, was chosen to elicit catalytic antibodies. As this approach, eliciting catalytic antibodies to a stable ground state metal binding hapten, as opposed to a transition state hapten, is novel, it was necessary to choose chemical compounds which were easily assayed and chemically manipulated. While 7-hydroxy-4-methyl coumarin provides a fluorescent chromophore which can be easily assayed, a number of various coumarin derivatives could have been utilized (Pollack, S. J., et al., *Science*, 242:1038 (1988); Pollack, S. J., et al., *J. Am Chem Soc.*, 111:2282 (1989); and Baldwin, et al., *Science*, 245:1104 (1989)). In addition to assayable chromophores, p-nitrophenyl esters are also easily assayed. The anion cleavage product, p-nitrophenolate, is yellow at basic pH, and its appearance can be followed spectrophotometrically at 405 nm. The chemical compounds discussed above and used in hapten 100 were helpful in tracking the catalytic activity of the resulting antibodies, however, other chemical compounds which can not be assayed may certainly be used. Thymidine was chosen as the nucleotide component because it can be easily manipulated chemically. The hapten described above was used to generate monoclonal antibodies that would hydrolyze a substrate having a natural phosphate diester bond, such as that present in DNA, shown in FIG. 4.

Figure 5:
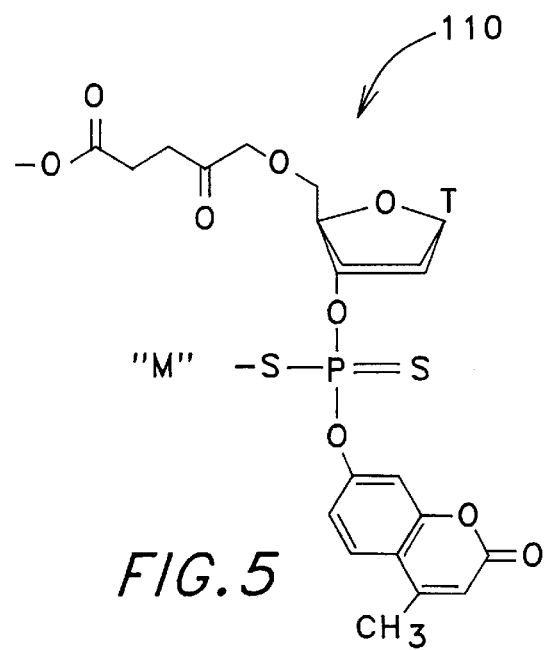
FIG. 5 is a schematic representation of the structure of a phosphorodithioate hapten chelate of the present invention.

Hapten 100 was synthesized using the method of Yau, E. K., et al., *Tetrahedron Letters*, 31:1953–1956 (1990), with minor modifications, to be discussed in detail below, and coupled to the carrier proteins bovine serum albumin (BSA) and keyhole limpet hemocyanin (KLH) thereby forming an antigen. Metal ion antigen chelates 110, shown in FIG. 5, were formed by incubating the BSA conjugate with metal ions and performing exhaustive dialysis to remove the excess metal.

These putative complexes were subject to atomic absorption spectroscopy to determine the amount of metal ions $Ag^{1+}$, $Hg^{2+}$, as well as the tris-N,N,N-(2-aminoethyl)amine (tren) chelate of $Co^{2+}$($Co-N_4$ compounds). The [$Co-N_4$] compound had been previously shown to hydrolyze activated phosphodiester compounds by Chin, J., et al., *J. Am. Chem. Soc.*, 111:186 (1989); however, this "antigen chelate" was not effective for generating catalytic antibodies via the process of this invention. Metal ion/phosphorodithioate ratios were 2:1, 1:1, and 0.9:1 for $Hg^{2+}$, $Ag^{1+}$, and $Co^{2+}$, respectively. As it was anticipated that other metal ions could similarly chelate with the dithioate hapten, immunizations were also performed using putative chelates of hapten metals $Ni^{2+}$ and $Zn^{2+}$. It is to be understood that the present invention is not limited to the metal ions discussed above as other metal ions such as $Cu^{1+}$, $Cu^{2+}$, $Cd^{2+}$, $Fe^{1+}$, $Fe^{2+}$, $Mn^{2+}$, $Mg^{2+}$, etc. would also suffice.

Figure 6A:
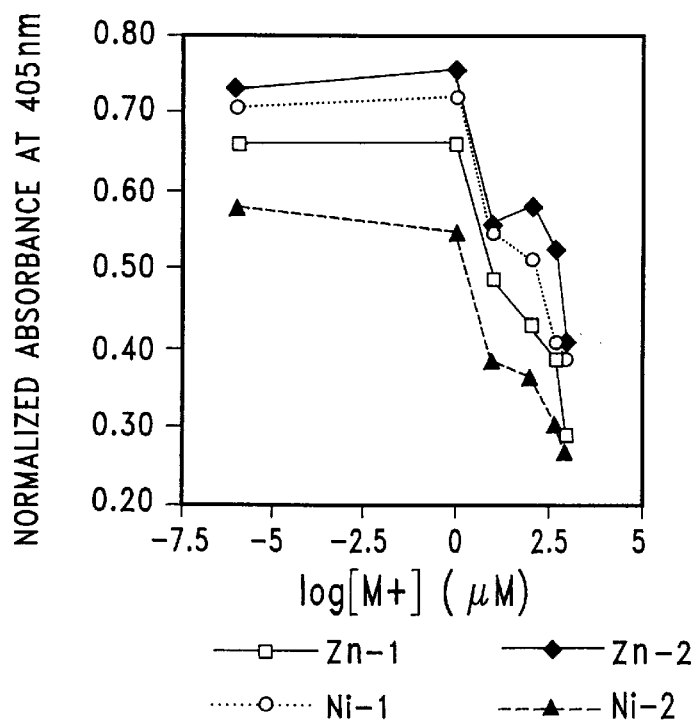
FIG. 6a is a graphical representation of a metal ion competition with enzyme-linked immunosorbent assay (ELISA) with the same metal ions used in the hapten-metal chelates injected into mice.
Figure 6B:
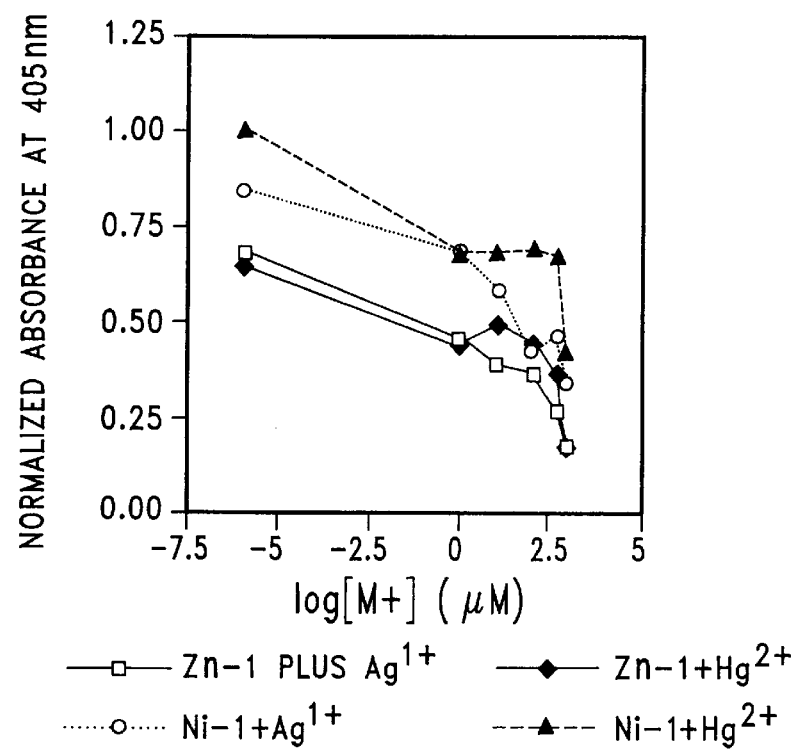
FIG. 6b is a graphical representation of a metal ion competition with enzyme-linked immunosorbent assay (ELISA) with $Ag^{1+}$ or $Hg^{2+}$.

Monoclonal antibodies were generated from hosts, that is, mice immunized with antigen chelate 110, wherein M is $Ag^{1+}$, $Hg^{2+}$, $Ni^{2+}$, or $Zn^{2+}$. The skilled person in the art will recognize that a variety of antibody production methods have currently become available both in the literature and commercially, such as engineering antibodies from mRNA, bacterial libraries, or recombinant phage systems (McCafferty, J., et al., *Nature*, 348:552 (1990); Winter, G., et al., *Nature*, 349:293 (1991); and Recombinant Phage Antibody System, a kit manufactured by Pharmacia Biotech). The particular method of amplifying antibodies is not essential to the process of the present invention. The present invention utilized hybridoma technology. Selection of monoclonals was accomplished with enzyme-linked immunosorbent assay (ELISA). The ELISA is a sensitive technique for the detection of an antibody-antigen complex. The antigen is attached to a 96-well plate. A sample containing primary antibody is bound to the antigen. An anti-antibody conjugated to a reporter, such as alkaline phosphatase (AP), is then bound to the primary antibody and a substrate complimentary to the reporter is added, hence an AP substrate is added in the present case. The amount of substrate converted to product indicates the level of primary antibody bound from the original sample. In a competition ELISA, free antigen is added to the plate after the addition of primary antibody. The free antigen should compete with the antigen bound to the plate for primary antibody. The consequences would be a lowered response due to the binding of less primary antibody to the plate. Serum from twelve mice, (three immunized with the antigen chelate 110, wherein M is $Ag^{1+}$; five immunized with the antigen chelate 110, wherein M is $Hg^{2+}$; two immunized with the antigen chelate 110, wherein M is $Ni^{2+}$; and two immunized with the antigen chelate 110, wherein M is $Zn^{2+}$) were effectively competed by free antigen. All mice produce antibodies capable of antigen binding. Polyclonal serum from mice immunized with the antigen chelates 110, discussed previously, was found to bind metal ions. This was demonstrated by performing competition ELISA experiments with free metal ions $Ag^{1+}$, $Zn^{2+}$, $Hg^{2+}$, $Ni^{2+}$, shown in FIG. 6. The antibodies isolated were of the IgG class: Antibodies belong to one of five classes IgA, IgD, IgE, IgM, and IgG. IgG antibodies constitute the major class immunoglobulin in the blood.

After fusion, and initial growth of hybridomas, tissue culture supernatant containing secreted antibody was assayed for binding to the hapten by ELISA, by competition ELISA using free hapten, and by competition ELISA with $Ni^{2+}$. Those antibodies with the best combination of responses were cloned. After cloning, stable hybridoma lines were selected for expansion based on binding of antibody to hapten determined by ELISA only. The results of some of these ELISA's are shown in Table 1.

TABLE 1

| hybridoma | clone | ELISA response | hybridoma | clone | ELISA Response |
|---|---|---|---|---|---|
| 2G3 | C2 | 0.595 | 19G10 | B6 | 0.807 |
|  | C3 | 0.253 |  | C4 | 0.148 |
|  | D1 | 0.431 |  |  |  |
| 3A11 | A7 | 0.057 | 13E1 | B7 | 0.751 |
|  | F1 | 0.298 |  | C5 | 0.512 |
|  |  |  |  | C7 | 0.176 |
|  |  |  |  | D4 | 0.299 |
| 6A1 | A6 | * | 14E5 | A8 | 1.067 |
|  |  |  |  | C5 | 0.671 |
| 8B3 | B4 | 0.883 | 16D5 | B5 | −0.016 |
|  | C3 | 0.418 |  | D2 | 0.161 |
|  | B4 | 0.992 |  | D3 | 0.707 |
|  | C3 | 1.606 |  |  |  |

TABLE 1-continued

| hybridoma | clone | ELISA response | hybridoma | clone | ELISA Response |
|---|---|---|---|---|---|
| 10C12 | A8 | 0.142 | 20BT | A8 | 0.343 |
|  | C3 | 0.319 |  | D2 | 0.467 |
|  | D4 | 0.217 |  |  |  |
| 10H11 | A7 | 0.847 | 22C12 | B3 | * |
|  | B5 | 0.028 |  |  |  |
|  | B6 | 1.216 |  |  |  |
|  | E1 | 0.095 |  |  |  |
| 12E3 | D3 | * | 22H1 | A9 | 0.257 |
| 13A11 | A8 | 0.186 | 23A7 | B5 | 0.498 |
|  | D3 | 0.199 |  | C3 | 0.926 |
|  |  |  |  | D2 | 0.554 |
| 13C9A6 | A6 | 0.877 | 24B8 | B5 | 1.188 |
|  |  |  | 24C2 | C5 | 0.167 |
|  |  |  | 24H3 | A7 | −0.028 |

*The response for this ELISA was not quantitated. The clone was selected by inspection.

The highest responding clone for each hybridoma, shown in boldface, was selected for expansion. After the expansion, 12 cell lines were judged stable and were used for subsequent catalytic experiments. These cell lines are shown in Table 2.

TABLE 2

| 3A11F1 | 6A1A6 | 8G3C3 | 10C12C4 |
|---|---|---|---|
| 10H11B6 | 12B3D3 | 19G10B6 | 20B7D3 |
| 22C12B3 | 23A7C3 | 24B8B5 | 24C2C5 |

Some hybridoma lines produced very low amounts of antibody which were insufficient to conduct the experiments. Others were very poor producers of ascites fluid. For these reasons, not all antibodies were tested for catalytic activity.

To confirm the existence of catalytic activity for the monoclonal antibodies, the following compounds were used as substrates and the results will be discussed in the Examples that follow: Thymidine 3'-O-(7-hydroxy-4-methyl coumarin) phosphodiester and related compounds; p-nitrophenyl esters; adenosine triphosphate; and various deoxyoligonucleotides.

In a second embodiment of the present invention, the method of the preferred embodiment described above is used to generate catalytic antibodies that will neutralize various nerve gases. Many of the most toxic nerve gases such as tabun, sarin and parathion are phosphorous derivatives. These compounds preferably, or their sulfur derivatives would be stabilized as discussed previously, coupled to a carrier protein and incubated with metal ions to form metal ion-hapten chelates. Other sulfur containing analogues of these nerve gases may also serve as haptens. Immunizations would then be carried out using these antigen chelates, and monoclonal antibodies isolated and identified in a manner similar to that described in detail below.

All of the catalytic antibodies to date have been based on the thymine 3'-O-(7-hydroxy-4-methyl coumarin) phosphodithioate chelate or hapten 100. The invention is further illustrated by the following non-limited examples. All scientific and technical terms have the meanings as understood by one with ordinary skill in the art. The specific examples which follow illustrate the synthesis of representative haptens or compounds that are used to generate the catalytic antibodies of the present invention. The methods may be adapted to variation in order to produce haptens and antibodies embraced by this invention but not specifically disclosed. Further variations of the methods to produce the same haptens and antibodies in somewhat different fashion will be evident to one skilled in the art.

Reagents and Methods

All reagents were used as received unless otherwise noted. All solvents were obtained as anhydrous. All reagents were obtained from Aldrich or Mallinckrodt Chemical Co., except the following: 2,4-Dichlorobenzyl mercaptan was obtained from Lancaster Chemicals. 5'-O-Dimethoxytritylthymidine-3'-O-[($\beta$-cyanoethyl)-N,N-diisopropyl]-phosphoramidite or starting compound (a) shown in FIG. 7 was obtained from Glen Research at 44901 Falcon Place, Sterling Va. 20166. 4-Dimethylaminopyridine (DMAP) was obtained from Glen Research as a 6.5% (w/v) solution in tetrahydrofuran. Methylimidazole (MeIm) was obtained from Glen Research as a 10% solution in tetrahydrofuran (THF). Tetrazole was obtained from Glen Research as a 0.45 M solution in acetonitrile ($CH_3CN$). Trichloroacetic acid (TCA) was obtained from Glen Research as a 3% (w/v) solution in methylene chloride ($CH_2Cl_2$). Water ($H_2O$) was deionized.

Thymidine 3'-monophosphate p-nitrophenyl ester was prepared according to the method of Turner and Khorana (Turner, A. F., et al., *J. Am. Chem. Soc.*, 81:4651 (1959)). Thymidine 5'-monophosphate phenyl ester was obtained from Dr. Peter Seeberger, Memorial Sloan-Kettering Cancer Center, Laboratory for Bioorganic Chemistry, 1275 York Avenue, New York, N.Y. 10021, and is available from Dr. Marvin Caruthers, Department of Chemistry and Biochemistry, University of Colorado, Boulder, Colo. 80309.

NMR. $^1$H NMR were recorded on a Varian VXR-300S in the solvent indicated. $^{31}$P NMR spectra were recorded on a Bruker AM-400 spectrometer operating at 121.4 Hz with broad band decoupling referenced to 85% $H_3PO_4$ as an external standard.

Flash Column Chromatography. Flash chromatography was performed using silica gel 60 from VWR Scientific. The amount of silica gel used was determined using the rule "100 g silica gel for 1 g compound".

Thin Layer Chromatography (TLC). Thin layer chromatography was performed using silica gel 60 $F_{254}$ with aluminum backing manufactured by EM Science. Preparative TLC was performed using 20×20 cm glass plates coated with silica gel 60, 2 mm thick, manufactured by EM Science.

Storage Buffer. Purified antibodies were stored in 1 mM HEPES, 150 mM NaCl, pH 7.2–7.4.

Protein Assays. Protein concentrations were determined by the method of bicinchoninic acid assay (Smith P. K., et al., *Analytic Biochemistry*, 150:76 (1985)). Copper (11) Sulfate pentahydrate (4% w/v) solution was added to bicinchoninic acid at a ratio of 1:50 to produce a working reagent. These solutions were available in kit form from several suppliers. 200 $\mu$L of working reagent was added to 10 $\mu$L of sample in a microtiter plate. The assay was allowed to develop for 30 minutes at 37° C. and the absorbance at 562 nm is read using a Molecular Devices Vmax® microplate reader.

Dialysis. Antibody solutions were dialyzed for at least six hours to effect a buffer exchange. Exhaustive dialysis was defined as a $10^6$-fold dilution of sample buffer. Concentration. Antibody solutions were concentrated using centrifugal concentrators available commercially with somewhat of a loss in yield. Alternatively, concentration was effected by the method of Scopes (Scopes, R. K., *Protein Purification Principles and Practices;* 2nd edition; Springer-Verlag: New York, Pg. 329, (1987). Antibody solution was placed in dialysis tubing and the tubing was coated with polyethylene glycol compound (MW≈20,000, Sigma Chemical company, #P-2263). PEG attracts buffer from the bag. With high water activity outside the bag and low water activity inside, the water was forced out. Wet PEG was stripped from the outside of the bag and the process was repeated until the desired volume is reached. Care must be taken to prevent drying of the sample which renders the antibody inactive.

IgG Purification

Protein A Chromatography. This protocol was adapted from that of Fredriksson, et al. It has been optimized for purification of monoclonal antibody 6A1A6.

Buffers used for purification of IgG's are summarized in Table 3 below (Note: all buffers were filtered and degassed prior to use on the FPLC system).

TABLE 3

| | |
|---|---|
| Binding buffer: | 1.5 M glycine, 3 M NaCl, pH 8.9 |
| Elution buffers: | A: 0.1 M citric acid, pH 6.0 |
| | B: 0.1 M citric acid, pH 3.0 |
| Collection buffer: | 1 M Tris·Cl, pH 9.0 |
| Regeneration buffer: | 1.5 M NaSCN |
| Storage buffer: | 10 mM $Na_2HPO_4$, 150 mM NaCl, pH 7.2, 0.05% $NaN_3$ (w/v) |

A 10 mL sample of ascites fluid was added to 20 mL binding buffer and the solution clarified by centrifugation at 10,000 g for 15 minutes. The solution was further clarified by filtration through a glass wool plug to remove all lipids and particulates. The solution was applied to a 10 mL column of Protein A Sepharose CL-4B (Pharmacia, #17-0963-03) that was previously equilibrated with 50 mL binding buffer. All flow rates were 2.5 mL/min. The column was washed until the absorbance of the eluant at 280 nm returned to baseline value. Antibody was eluted using a step pH gradient as follows: 11 minutes with 100% A (pH 6.0), 11 minutes with 67% B (pH 4.0), and 11 minutes with 100% B (pH 3.0). At the pH 4.0 step, 2.5 mL fractions were collected into tubes containing 0.8 mL collection buffer. This immediately neutralizes the eluting antibody. The column was then regenerated with five column volumes of regeneration buffer followed by two columns of storage buffer. Fractions from the pH 4 elution containing antibody were pooled and dialyzed against the desired buffer and concentrated.

Anion-Exchange Chromatography. Anion-exchange chromatography was performed with a Pharmacia 5/5 MonoQ column which contains quaternary amino groups.

Buffer A: 20 mM Tris·HCl, pH 7.8.

Buffer B: 20 mM Tris·HCl, 1 M NaCl, pH 7.8.

To a Protein A purified solution of antibody (150 mM NaCl) buffer A was added such that the NaCl concentration was reduced to 40 mM. The solution was applied to the column at 1 mL/min. Elution was effected with a step-wise gradient at a flow rate of 1 mL/min. as follows: 4% to 8.5% B over 8 minutes, 8.5% B for 8 minutes, 8.5% to 15% B over 7 minutes and 15% B for 12 minutes. IgG typically elutes at 150 mM NaCl (15% B). The column was regenerated with 100% B prior to the next injection, requilibrated with 100% A, and stored in 20% ethanol.

Cation-Exchange Chromatography. Cation-exchange chromatography was performed with a Pharmacia 5/5 MonoS column.

Buffer A: 50 mM MES, pH 6.

Buffer B: 50 mM MES, 1 M NaCl, pH 6.

To a Protein A purified solution of antibody (150 mM NaCl) buffer A was added such that the NaCl concentration was reduced to 1.5 mM. The solution was applied to the column at a flow rate of 1 mL/min. Elution was effected with a gradient of 0–20% B over 20 minutes at a flow rate of 1 mL/min. IgG typically elutes at 12–18% B (6–9 mM). The column was regenerated with 100% B prior to the next injection, requilibrated with 100% A, and stored in 20% ethanol.

$F_{ab}$ Fragments. $F_{ab}$ fragments or antigen binding fragments were prepared according to the method described in Harlow and Lane, discussed previously. Concentrated solutions of antibody (5 mg/mL) were recommended; however, usually solutions of about 2 mg/mL were used with success. The antibody was either dialyzed against 100 mM sodium acetate, pH 5.5 or 3 M sodium acetate pH 5.5 was added to the antibody sample to achieve a final concentration of 100 mM. To this solution was added 1/20 volume of cysteine from a 1 M stock (final concentration is 50 mM) and 1/20 volume of EDTA from a 20 mM stock (final concentration is 1 mM). Addition of DTT was found to be beneficial: typical concentration was 2 $\mu$M. Papain was added at 10 $\mu$g per mg of antibody. The reaction was allowed to proceed for six hours at 37° C. or at room temperature. Iodoacetamide was added to a final concentration of 75 mM and the reaction was incubated for 30 minutes at room temperature. The $F_{ab}$ fragments were purified by protein A chromatography.

Sodium Dodecyl Sulfate Polyacrylamide Gel Electrophoresis (SDS PAGE).

Solutions and buffers used for SDS PAGE are summarized below in Table 4.

TABLE 4

| | |
|---|---|
| 25% Acrylamide (40:1): | 25 g acrylamide, 0.625 g bis-acrylamide in 100 mL $H_2O$. |
| 2X Stacking Gel Mixture: | 0.25 M Tris HCl, 0.2% sodium dodecyl sulfate (SDS), pH 6.8 |
| 2X Separating Gel Mixture: | 0.75 mM Tris.HCl 0.2% SDS, pH 8.8. |
| 5X Running Buffer: | 125 mM Tris.Cl, 1 M Glycine, 0.5% SDS, pH 8.3 |
| 2X Loading Buffer: | 125 mM Tris.Cl, pH 6.8, 2 g SDS, 1 mL $\beta$-mercaptoethanol, 2 mL glycerol, 0.05% dye markers in a total of 10 mL |

Gel Electrophoresis. Denaturing polyacrylamide gel electrophoresis was performed using the method of Laemmli (Laemmli, U. K, *Nature*, 227:680 (1970)). Gels consisted of a 12% separation gel (80% of the gel volume) and a 4% stacking gel (20% of the gel volume). A 12% gel was typically prepared by combining 19.2 mL of acrylamide stock, 20 mL of 2x Separating Mixture and 0.8 mL $H_2O$. The four percent gel was prepared in a corresponding manner. Polymerization was effected with the addition of 300 $\mu$L of 10% ammonium persulfate and 1/1000 volume of tetramethylethylenediamine (TEMED). The separating gel was poured first and a layer of n-butanol was poured on top of the gel until polymerization was complete. The butanol was removed, the separating gel was poured, and a comb inserted until polymerization was complete. Samples were diluted 1:1 with 2x Loading Buffer and heated at 90° C. for 5 minutes prior to loading onto the gel. Gels were run in 1x running buffer at 125V until the bromophenol blue dye reached the bottom of the gel. Alternatively, commercially available 8–16% gradient gels, Catalog No. EC6045, were used purchased from Novex Electrophoresis, 4202 Somerto Valley Blvd., Ste. B, San Diego, Calif. 92121.

Silver Staining. Gels were typically silver stained to visualize protein bands. This procedure was adapted from Harlow and Lane, discussed previously. The gel was fixed in 50% methanol, 12% acetic acid for greater than one hour, typically overnight. The gel was washed with 50% methanol three times for twenty minutes each. The gel was treated with a solution of $Na_2S_2O_3$ (0.1 g/L) for one minute. The gel was rinsed three times with deionized water and stained with a solution of 0.1% of $AgNO_3$ (diluted from a 20% stock) and formaldehyde at 0.75 mL/L for twenty minutes. The gel was rinsed 3–7 times with deionized water and developed with a solution of 6% $Na_2CO_3$, 1 mg/L $Na_2S_2O_3$, and 0.5 mL/L formaldehyde. When bands were developed, the developing solution was removed and water added. After twenty minutes, the gel was transferred to 1% acetic acid to stop the developing reaction. Gels were either dried or photographed.

Kinetic Assays

General. Because antibody 6A1A6, see Table 2, was metal dependent, a few precautions were taken to insure consistent results for all assays. Variable background catalysis was observed in each prep and was presumably due to the presence of metal ions in the antibody solutions. EDTA was added to reactions to a concentration that removed the catalytic activity. $MgCl_2$ or other metal salts were then added back to the reactions at the optimum level. Antibody concentration was adjusted for each system to obtain useable data in a reasonable reaction time and varied from 0.5–4 $\mu$M.

Kinetic analyses were done by standard methods as described. Rates were defined as initial velocities and reported in $min^{-1}$ or $sec^{-1}$. Each assay was done in duplicate or triplicate to allow for error analysis. Background rates were measured using an identical reaction mixture without antibody present. Michales-Menten parameters $k_{cat}$ and $K_m$ were derived from Eadie-Hofstee or weighted Lineweaver-Burk plots (using the computer program Enzyme Kinetics 1.0, Macintosh, Trinity Software). Inhibitory constants, $K_i$, were derived from Dixon or Lineweaver-Burk plots.

EXAMPLE I

Figure 7:
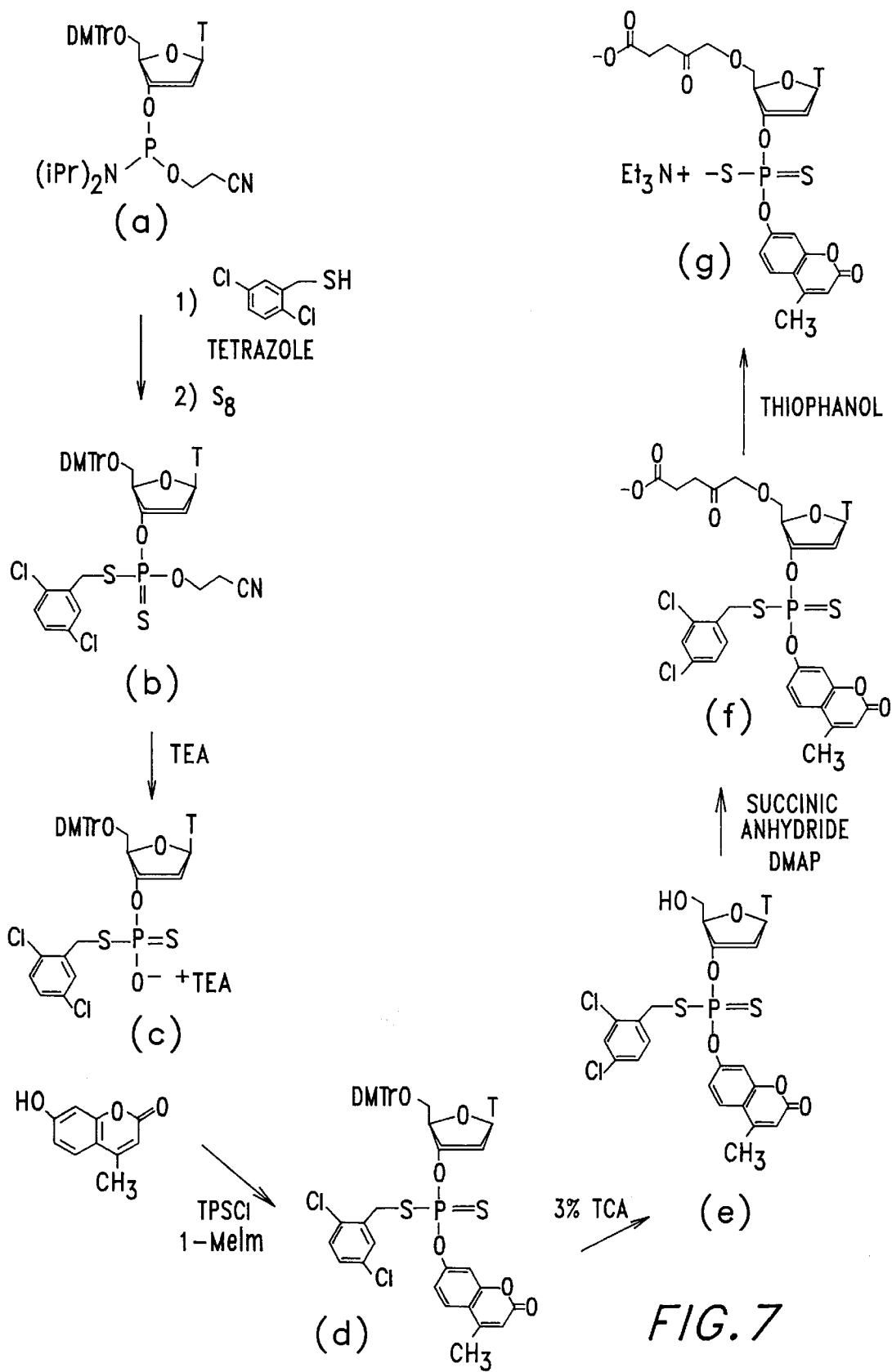
FIG. 7 is the synthesis scheme for a hapten useful for the present invention.

Preparation of 5'-O-Succinylthymidine-3'-O-(7-Hydroxy-4-Methyl Coumarin) Phosphorodithioate·$Et_3$N to be used as Haptens The following steps for the preparation of 5'-O-succinylthymidine-3'-O-(7-hydroxy-4-methyl coumarin) phosphorodithioate·$Et_3$N are schematically represented in FIG. 7, and is an adaptation of Yau, E. K., et al., discussed previously.

(a). 5'-O-Dimethoxyritylthymidine-3'-O-[($\beta$-Cyanoethyl)-S-2,4-Dichlorobenzyl)] Phosphorodithioate or intermediate (b). 2,4 Dichlorobenzyl mercaptan (3.3 eq., 8.84 mmol, 1.14 ml) and tetrazole solution (2.4 eq., 6.4 mmol, 14 mL) were added to starting compound (a) (2.00 g, 2.68 mmol) in 5 mL $CH_3CN$ and the reaction was stirred at 25° C. for 50 minutes. Sulfur (5% solution in 1:1 $CS_2$/pyridine (v/v), 9.38 mmol, 6 mL, 3.5 eq.) was added and the solution was stirred for 1 hour. The solution was diluted with EtOAc and washed with 5% $NaHCO_3$ (2×50 mL) and saturated NaCl solution (50 mL). The organic layer was dried ($Na_2SO_4$) and evaporated. The residue was dissolved in a minimal amount of EtOAc and precipitated into pentane. The resulting white/yellow precipitate intermediate (b) was coevaporated with $CH_3CN$. Yield: 2.139 g (2.46 mmol, 92%).

(b). 5'-O-Dimethoxytritylthymidine-3'-O-(S-2,4-Dichlorobenzyl) Phosphorodithioate $Et_3$N or intermediate (c). $CH_3CN$ (8.8 mL) and $Et_3$N (8.8 mL) were added to intermediate (b) (2.139 g, 2.46 mmol) (resulting in a 0.14 M solution of intermediate (b)) and the reaction was stirred for 4 hours at 25° C. The reaction solution was evaporated and the residue purified by flash chromatography (eluting solvent: $CH_2Cl_2/CH_3OH/Et_3N$ (95:3:2). Fractions containing product ($R_f$: 0.4) were pooled and the solvent evaporated to afford intermediate (c) as a yellow foam. Yield: 1.65 g (1.85 mmol, 62%). $^{31}P$ NMR: 75.1, 73.4 ($CDCl_3$).

(c). 5'-O-Dimethoxytritylthymidine-3'-O-(7-Hydroxy-4-MethylCoumarin)-(S-2,4-Dichlorobenzyl)] Phosphorodithioate or intermediate (d). 4-hydroxy-7-methyl coumarin (1.5 eq, 1.32 mmol, 233 mg,) triisopropyl sulfonyl chloride (TPSCl) (3 eq., 2.64 mmol, 800 mg), and MeIm (5 eq., 4.40 mmol, 0.361 g, 351 µL) were added to intermediate (c) (807 mg, 880 µmol) in pyridine (12 mL) and the reaction stirred at 25° C. for six hours at which point TLC ($R_f$: 0.83; hexane/EtOAc (2:8)) showed the reaction was complete. The solvent was evaporated and the residue dissolved in a minimal amount of $CH_2Cl_2$ and purified by flash chromatography (Eluting solvent: Hexane/EtOAc (2:8)) to afford intermediate (d) as a light yellow foam. Yield: 300 mg, 308 µmol, 35%. $^{31}P$ NMR: 96.98 ($CD_3CN$).

(d). Thymidine-3'-O-[(7-Hydroxy-4-Methyl Coumarin)-S-2,4-Dichlorobenzyl)] Phosphorodithioate or intermediate (e). A 3% (w/v) solution of trichloroacetic acid in dry $CH_2Cl_2$ (10 mL) cooled to 4° C. was added to intermediate (d) (300 mg, 308 µmol) and cooled to 0° C. After 45 minutes 10 mL of a solution of pyridine/$CH_3OH$ (1:1 (v/v)) was added and the solution stirred at 25° C. for 15 minutes. The reaction mixture was extracted with 5% $NaHCO_3$ (1×100 mL), then dried ($Na_2SO_4$). The solvent was evaporated and the residue coevaporated with toluene. The resulting gum was dissolved in $CH_2Cl_2$ and purified by flash chromatography (Eluting solvent: EtOAc) to yield intermediate (e) ($R_f$: 0.28) as a white foam. Yield: 105 mg (157 µmol, 51%). $^{31}P$ NMR: 92.38, 92.07, ($CDCl_3/CH_3OH$).

(e). 5'-O-Succinylthymidine-3'-O-[(7-Hydroxy-4-Methyl Coumarin)-(S-2,4-Dichlorobenzyl)] Phosphorodithioate or intermediate (f). Succinic anhydride (10 eq., 1.57 mmol, 158 mg) and DMAP solution (0.1 eq., 15.0 µmol, 2.0 mg, 28 µL) were added to intermediate (e) (105 mg, 157 µmol) in pyridine (1 mL) and the reaction stirred at 25° C. for ≈90 minutes at which point TLC ($R_f$: (EtOAc/$CH_3OH$ (85:15)), 0.38) showed the reaction was nearly complete. The solvent was evaporated and the residue coevaporated with toluene (2×). The resulting gum was purified by flash chromatography (eluting solvent: EtOAc/$CH_3OH$ (85:15). The product intermediate (f) ($R_f$: 0.5) was obtained as a clear glassy material. Yield: 115 mg (149 µmol, 95%). $^{31}P$ NMR: 92.74, 92.55 ($CD_3CN/CH_3OH$).

(f). 5'-O-Succinylthymidine-3'-O-(7-Hydroxy-4-Methyl Coumarin) Phosphorodithioate·$Et_3N$ or product (g). Thiophenol/dioxane/$Et_3N$ (1:2:2, (v.v), 5 mL) was added to (f) (115 mg, 149 µmol) and the reaction stirred at 25° C. for 4.5 hours at which point TLC showed that the reaction was nearly complete ($R_f$: 0.1, ($CH_2Cl_2$/iPrOH (65:35))). The solution was concentrated to a minimal volume and applied to a preparative TLC plate (eluting solvent: $CH_2Cl_2$/iPrOH (65:35)). The band corresponding to the product (g) was scraped off the TLC plate, crushed to a fine powder and the product eluted with iPrOH. The iPrOH was evaporated and the product (g) was recovered as a yellowish gum. Yield: 50 mg (70 µmol, 47%). Overall Yield: 4.9%. $^{31}P$ NMR: 113.63 (d6-acetone). Mass spectroscopy (FAB-): Matrix was Nitrobenzyl alcohol (NOBA). (M-1) 611 (free anion); (M-1) 714 (salt). UV spectroscopy: maxima at 272λ and 314λ.

EXAMPLE II

Production of Monoclonal Antibodies to the Hapten of the Present Invention

Most of the steps in monoclonal antibody production have been analyzed in detail and are considered to be routine to one skilled in the art, as evidenced by the presence of many manuals describing the procedures. However, below is a detailed discussion of this procedure.

(a). Antigen Preparation

This protocol was adapted from those of Oliver and Steiner (Oliver, J., Clin. Invest., 47:1306 (1968); and Steiner, PNAS, 64:368 (1969)). To bovine serum albumin (BSA) Fraction V, in 1 mL $H_2O$ (2.5 mg, 0.038 µmol, 0.1 eq.) was added hapten synthesized according to the present invention (2 mg, 3.8 µmol, 2 eq) and 1-ethyl-3-(3-dimethylaminopropyl) carbodiimide (EDC) (2.2 mg, 11.4 µmol, 3 eq.). The pH of the solution was adjusted to 5.5–6.0 after each addition with 1M HCl, and again after 30 minutes of incubation. After one hour additional EDC was added (1.5 mg, 7.6 µmol, 2 eq.) and the pH adjusted again. The reaction was incubated at room temperature and allowed to proceed overnight. The reaction was dialyzed against phosphate buffered saline (10 mM $Na_2HPO_4$, 150 mM NaCl, pH 7.2).

The hapten/protein ratio (epitope density) was determined by measuring the electronic spectrum of the conjugate and calculating the concentration of hapten using $\lambda_{max}$=315 nm and $\in$=13,000. BSA concentration was determined by the bicinchoninic acid assay (BCA) assay, discussed previously in the Reagents and Methods section. The keyhole limpet hemocyanin (KLH) conjugate was prepared similarly except that the reaction pH was 6.5.

(b). Immunizations

This protocol was adapted from the Ribi adjuvant system as supplied by RIBI ImmunoChem Research, Inc., P.O. Box 1409, Hamilton, Mont. 59840. The vial of adjuvant w a s reconstituted with 0.5 mL sterile PBS to yield a solution that was 4× the suggested concentration. The reconstitution was performed by warming the vial in hot water for 5–10 minutes, adding PBS and vortexing vigorously for 2–3 minutes to form an emulsion. A 4× solution (4 mM) of metal ion was prepared in sterile PBS. The antigen solution was also prepared in sterile PBS. These solutions were mixed immediately prior to the immunization to yield final concentrations of 1 mM metal ion, 1× adjuvant, and 25 µg antigen per 100 µL injection volume. The solution was vortexed vigorously to ensure that an emulsion was formed.

100 µg of antigen is considered a normal dose for immunizations; however, the antigen dose was reduced to 25 µg in some cases. The mice to be immunized were swabbed across the back with 20% ethanol, and the antigen administered subcutaneously through a 24 gauge needle. This is defined as day zero. Boosts were performed on days 7 and 21. A test bleed (see below) was performed on day 26. The mice were hyperimmunized on day 31, and the fusion was performed on day 35.

(c). Test Bleeds

The mouse was warmed with a heat lamp until it rubbed its face with its paws. This dilates the blood vessels. The mouse was then placed in a restraint or held firmly. One of the four tail veins was cut with a razor blade. Five to fifteen drops of blood were collected in a tube. The blood was allowed to stand at room temperature for about thirty minutes, until a clot formed. The clot was removed from the tube and the tube centrifuged to remove any remaining red blood cells from the serum.

(d). Enzyme-Linked Immunosorbent Assay (ELISA)

All Buffers and solutions used in the ELISA assay are summarized in Table 5 below. 100 µL of (1 µg/100 µL)BSA-hapten conjugate was added to each well of a 96 well ELISA plate and the plate incubated at 4° C. overnight. The solution was removed and the wells rinsed three times with PBS-Tween. The wells were saturated with blocking buffer and the plate incubated for two hours at room temperature. The solution was removed and the plate not rinsed. Primary antibody (from serum, cell supernatant, etc.) was added at 100 μL/well (solutions are diluted in blocking buffer) and incubated two hours at room temperature. The wells were emptied and washed with PBS-Tween. 100μL of alkaline phosphatase-conjugated anti-antibody diluted appropriately was added to each well and the plate incubated at room temperature for two hours. The solution was removed and the wells filled with a solution of p-nitrophenyl phosphate (1 mg/mL) in diethanolamine buffer and the absorbance at 405 nm measured for each well. For assays involving metal ions, the metal ions were added after the overnight incubation.

The plate was incubated for ½ hour at room temperature and the metal ion solutions removed. Serum samples were diluted 1:100, 1:500, 1:1,000, 1:5,000, 1:10,000, and 1:50,000 and the observed ELISA responses plotted at absorbance vs. $\log_{serum\ dilution}$. The free carrier protein was also assayed under the same conditions and compared to the hapten-protein conjugate.

Hapten competition assays were performed as follows: a serum dilution was chosen that did not contain saturating amounts of antibody based on the above analysis. For each mouse a dilution was chosen such that the ELISA response was normalized across all mice. The serum was incubated with concentrations of hapten that were 0.1-, 1-, 10-, 100-, and 500- fold of that coated to the plate. The ELISA was performed as above, and the data was plotted as normalized ELISA response vs. $\log_{hapten\ concentration}$. Competition assays were also performed with metal ions in the same manner. A 10× concentration of hapten (inhibitory, but not totally) was used and $Ni^{2+}$, $Zn^{2+}$, $Ag^{1+}$, and $Hg^{2+}$ were titrated from 0–1 mM. Fusions were performed using the mice with the best combination of serum titer and inhibition by free hapten.

TABLE 5

| Coating buffer: | 1.59 g/L $Na_2CO_3$, 2.93 g/L $NaHCO_3$, 0.02% $NaN_3$ (w/v) |
|---|---|
| PBS-Tween*: | 8 g/L NaCl, 0.2 g/L $KH_2PO_4$, 2.9 g/L $Na_2HPO_4.12H_2O$, 0.2 g KCl, 0.5 mL Tween-20t, pH 7.4 |
| Blocking buffer: | PBS-Tween plus 1% BSA (w/v) |
| Diethanolamine (10%): | 97 mL/L diethanolamine, 0.2 g/L $NaN_3$, 100 mg/L $MgCl_2.6H_2O$, pH = 9.8 |

*In assays involving metal ions "Cl- free PBS-Tween was used to prevent metal ion precipitation. It was prepared using the phosphate salts instead of NaCl and KCl to an equivalent molar concentration.
tTween-20 is polyetnylene sorbitan monolaurate and is avaliable ftom Bio-Rad Laboratories.

(e). Polyethylene Glycol (PEG) Fusion (1) Myelomas. P3X63-Ag8.653 myelomas were used and are available from the American Type Culture Collection as cell repository line (CRL) 1580. These cells grow exponentially (log phase) when the cell density is between $3.5 \times 10^5$ cells/mL and $1 \times 10^6$ cells/mL. Media and solutions required for the fusion are described and defined below in Table 6. Cells must first be grown in HT medium containing $1 \times 10^{-4}$ M 8-azaguanine. HT medium is used to ensure optimal growth later in HAT medium. 8-azaguanine is an analog that is incorporated into the DNA of cells containing the HGPRT gene where it is toxic. The myelomas are HGPRT⁻ and selection with this analog insures that no HGPRT⁺ revertants are present. Cells are grown until about 150 mL of media is present. The cells are then transferred to a 1 L spinner flask, diluted with 100 mL HT medium with no 8-azaguanine and grown in suspension. The culture was checked daily by performing a viable cell count using trypan blue staining and a hemacytometer. Cells were expanded until the total amount of cells present was $3–5 \times 10^8$ cells. Once a fusion date was set, one can estimate when to expand myelomas based on the doubling time of 18 hours such that the required amount of cells is maintained.

TABLE 6

| Complete IMDM Medium: | 400 mL IMDM salts |
|---|---|
| | 100 mL Fetal Calf Serum* |
| | $5 \times 10^{-5}$ M β-mercaptoethanol† |
| | 100 μg/mL penicillin/streptomycin |
| Serium-Free IMDM Medium: | 400 mL IMDM salts |
| | $5 \times 10^{-5}$ M β-mercaptoethanol† |
| | 100 μg/mL penicillin/streptomycin |
| HT Medium: | Complete Media plus |
| | $1 \times 10^{-4}$ M hypoxanthine‡ |
| | $4 \times 10^{-7}$ M thymidine‡ |
| HAT Medium: | HT medium plus |
| | $1.6 \times 10^{-6}$ M Aminopterine§ |
| Macrophage Medium (MΘM)¹¹: | 350 mL IMDM salts and |
| | 50 mL commercially available |
| | hybridoma cloning factor (Origen)¹¹ |
| Dulbecco's $Ca^{2+}$ and $Mg^{2+}$, fee PBS#  | 2.68 mM KCl |
| | 1.14 mM $KH_2PO_4$ |
| | 137 mM $Na_2HPO_4$ |
| | 57.3 mM $Na_2HPO_4$ |
| Freeze Medium: | 250 mL IMDM salts |
| | 200 mL Fetal Calf Serum |
| | 50 mL DMSO |
| | $5 \times 10^{-5}$ M β-mercaptoethanol |
| | 100 μg/mL penicillin/streptomycin |

*Some fetal calf serum supports the growth of myeloma and hybridoma cells better than others. It is recommended that it be tested prior to use.
†β-mercaptoethanol is required for the culture of lymphoid cells as a reductant to regenerate redox enzymes.
‡Hypoxanthine and thymidine are substrates for the HPGRT salvage pathway. They are included in the media for myelomas because these concentration of "HT" may arrest a culture not previously adapted to HT containing media.
§HPGRT cells die in a medium containing aminopterine because the synthetic pathway for guanosine is blocked by this folic acid antagonist and the salvage pathway is unavailable. HPGRT+ (hybridoma) cells survive providing H and T are in the culture medium.
¹¹Hybridomas grow well in the presence of medium derived from mouse primary peritoneal macrophage cells. The use of MΘM eliminates the need for concurrent culture of other cells as "feeder layers".
PEG used for fusion binds $Ca^{2+}$ and probably other divalent cations, inhibiting fusion efficiency.

(2) PEG Solution for Cell Fusion. Merck PEG "gas chromatography grade" was used for fusion. A 50% solution of PEG was prepared by dissolving 5 g PEG in 5 mL $H_2O$ and rotating the tube at room temperature for one to two hours until it is dissolved. The clear solution was sterile filtered through a 0.2 μm filter and diluted with 0.5 mL tissue culture grade DMSO.

(3) Harvesting Splenocytes. The mouse was killed by cervical dislocation, rinsed thoroughly in Wescodyne (a potent germicide), and then rinsed in 70% ethanol. The mouse was placed on its right side in the top lid of a large petri dish. Using a pair of forceps the skin above the posterior of the mouse was lifted up, taking care to ensure that the skin was lifted away from the peritoneal lining. The raised skin was cut with scissors and the resulting flap of skin grasped firmly with forceps. While holding the mouse's tail, the skin was removed by tearing. The peritoneal lining was lifted free of the viscera and cut with scissors. The spleen was drawn out of the body cavity and fatty and connective tissue cut away.

The spleen was successfully transferred three times through 35 or 60 mm petri dishes containing 3 mL complete media. The spleen was then transferred to a dry petri dish and a small corner pinched off with forceps. Spleen cells were forced out of the opening by holding the intact end down with forceps and rubbing the spleen with another forceps toward the opened end. The dish was flooded with 5 mL complete media and the cells collected by repeatedly rinsing the dish with complete media. The rinses were collected in a single 50 mL centrifuge tube and centrifuged for five minutes at 1000 g. The cells were washed with 10 mL of serum free medium and once with Dulbecco's PBS. The cells were collected by centrifugation and resuspended in 10 mL of Dulbecco's PBS.

(4) Harvesting Myelomas. Myeloma cells should be healthy in appearance and in log phase. Cells were counted and media containing $1.2 \times 10^8$ cells was transferred to centrifuge tubes and pelleted by centrifugation at 1000 g for 5 minutes. The cells were resuspended in 10 mL complete media per tube and combined into one tube. The cells were centrifuged again and washed with 10 mL Dulbecco's PBS.

(5) Fusion. The spleen and myeloma cells were combined after gently resuspending each solution and the resulting solution divided into two tubes. The fusion was performed on each tube separately. The tube was centrifuged at 800 g for five minutes and the supernatant aspirated off as completely as possible. One mL of the PEG solution was removed from its container and added to the cell pellet while resuspending the cells by stirring with the end of the pipet. The stirring was continued for one minute. 10 mL of serum free medium was added with continued stirring to the solution as follows: 1 mL in one minute and the remaining 9 mL in two minutes. The cells were centrifuged at 400 g for 5 min. The supernatant was removed and the cells resuspended in 10 mL of complete IMDM. This was then diluted into 500 mL of MΘM supplemented HAT medium. This solution was dispensed into 28 96-well microliter plates at 200 µL per well with a multi-channel pipetor. The plates were placed in a 37° C., 5% $CO_2$ incubator.

(6) Selection and Expansion of Growth Wells. Colonies of cells were assayed by ELISA when the cell density was such that the media was acidified and had begun to turn yellow. The supernatant was removed from the wells and they were refilled with fresh media. Half of the supernatant was transferred to an ELISA plate well coated with BSA-hapten and half to a well coated only with BSA. ELISA positive wells were expanded by gently resuspending the cells in the positive well with a transfer pipet, removing nearly all the media and transferring it to a 24-well growth plate. The growth well was refilled with fresh media in case the expansion would fail and 1.5 mL of media added to the new expansion well. These expanded colonies were grown to confluence and the media screened by ELISA again for hapten-specific antibodies. At this point the cell lines that were judged to be the "best binders" by ELISA response and hapten inhibition were cloned.

(7) Cloning Cell Lines. The method used for cloning cells was single-cell cloning by limiting dilution adapted from Harlow and Lane (Harlow, E., et al., *Antibodies: A Laboratory Manual*; Cold Springs Harbor, N.Y., 1988). This procedure was performed twice to insure that the colonies were clonal.

100 µL of MΘM supplemented HAT medium was added to each well of a 96-well plate with a multi-channel pipettor. 100 µL of hybridoma cell suspension (in log phase) was transferred to the top left-hand well (A1) of a microtiter plate. The solution was mixed by pipetting. One in two doubling dilutions were performed down the left hand row of the plate. 100 µL from A1 was diluted into B1. After mixing, 100 µL from B1 was diluted into C1, etc. down to H1. 100 µL of fresh media was then added to column one and one in two doubling dilutions were performed across the plate (from column one to column 12) in the same manner using a multi-channel pipettor. Clones were ready to screen in approximately two weeks.

(8) Ascites Production. 0.5–1 mL pristane (2, 6, 10, 10-tetramethylpentadecane) per mouse was injected intraperitoneally (ip) two weeks prior to injection of cells. Glass syringes must be used as pristane will swell plastic syringes and make injection impossible. A 26-gauge needle is used to minimize leakage after injection.

Cells were grown such that there were enough cells to inject $1-2 \times 10^6$ cells per mouse. Typically three mice were injected at a time for each cell line. The cells were harvested while in log phase by centrifugation for 5 minutes at 1000 g. The medium was decanted and the cell pellet resuspended in 5 mL IMDM salts (no serum). The cells were pelleted again and resuspended such that there were $1-2 \times 10^6$ cells per 0.5 mL injection volume. The cells were then injected into the peritoneal cavity of mice previously primed with pristane as described above. In approximately two weeks the mice had developed soft tumors that were ready to tap. The tumor was rubbed with 20% ethanol, a 16-gauge needle inserted into the peritoneal cavity, and the ascites fluid drained into a centrifuge tube. The fluid was centrifuged at room temperature to pellet lipids and red blood cells, and the fluid stored frozen at −70° C. until ready for purification. Usually two or three taps could be performed before mice showed signs of poor condition at which time they were euthanized. Generation of ascites fluid was also accomplished at Affymax, Inc., and by Maine Biotechnology Services.

EXAMPLE III

Hydrolysis of Thymidine-5'-monophosphate-p-nitrophenyl Ester (pNPPT)

p-Nitrophenyl Esters as Substrates. A useful system to assess cleavage utilized substrates containing esters with p-nitrophenol leaving groups. This assay was fast, reproducible and much more trouble free than the fluorescence assays. It relied on the fact that the anion cleavage product, p-nitrophenolate, is yellow at basic pH and its appearance can be followed spectrophotometrically at 405 nm.

p-Nitrophenol-Containing Substrates. p-Nitrophenyl phosphate, disodium, hexahydrate was obtained from Sigma Chemical Company as "Sigma 104® Phosphatase Substrate" (catalog number 104-105) in 5 mg tablets. Thymidine 5'-monophosphate p-nitrophenyl ester was also purchased from Sigma (catalog number T4510). Thymidine 3'-monophosphate p-nitrophenyl ester was synthesized as described above. Also obtained from Sigma were p-nitrophenyl phenylphosphonate (catalog number N2131) and bis (p-nitrophenyl) phosphate (catalog number N3002).

Antibody 6A1A6 was assayed spectrophotometrically for its ability to cleave the above mentioned substrates containing the p-nitrophenyl leaving group at 405 nm using a Molecular Devices Vmax® kinetic microplate reader. Kinetic assays were performed in triplicate at 25° C. in 40 mM TAPS, 150 mM NaCl, 10 mM $MgCl_2$, 0.5–0.6 µM antibody, pH=9.0.

Figure 8A:
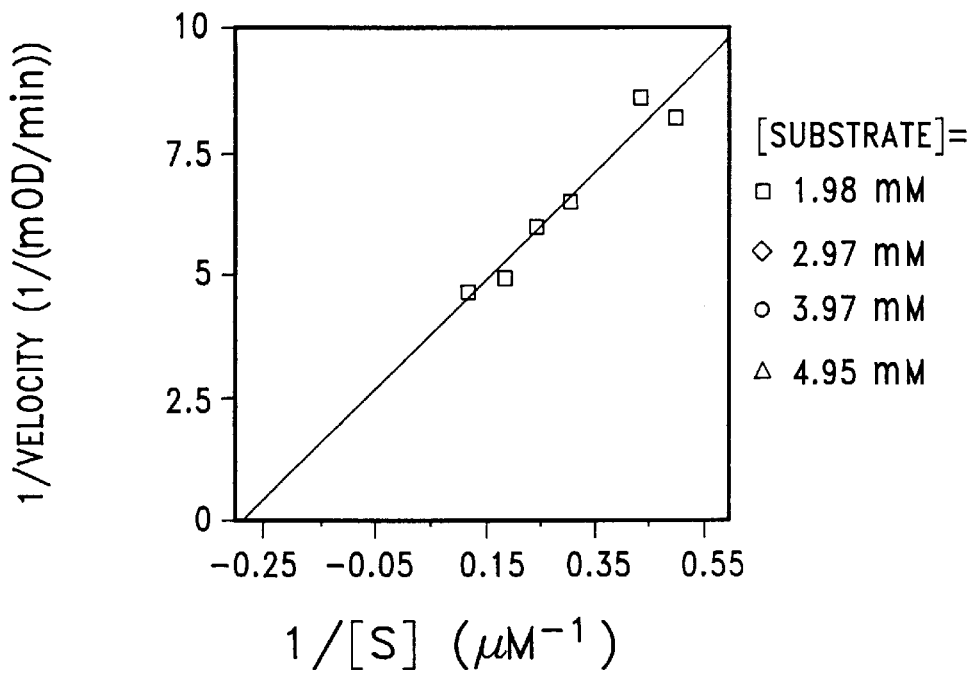
FIG. 8a is a double reciprocal plot for monoclonal antibody 6A1A6 with thymidine 5'-monophosphate p-nitrophenyl ester (pNPPT) as substrate.
Figure 8B:
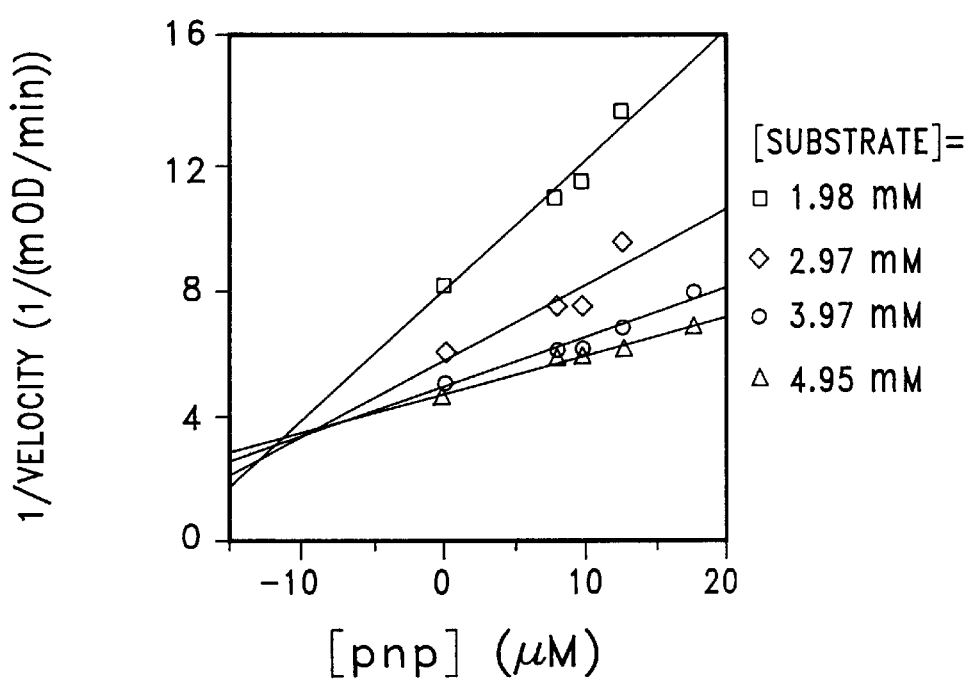
FIG. 8b is a Dixon plot of monoclonal antibody 6A1A6 reacting with 5'-monophosphate p-nitrophenyl ester (pNPPT) as substrate and p-nitrophenyl (pnp) as an inhibitor.

Phosphodiester Substrate. Antibody 6A1A6 of the present invention was found to catalyze the hydrolysis of thymidine-5'-monophosphate-p-nitrophenyl ester (pNPPT) in a metal dependent fashion. This represents the first report of a catalytic antibody capable of hydrolyzing a phosphodiester bond. pNPPT is normally used as a substrate for snake venom phosphodiesterase. The apparent values of $k_{cat}$ and $K_m$ with 10 mM MgCl$_2$ were 0.031±0.05 min$^{-1}$, and 0.29±0.08 mM, respectively. See FIG. 8a. The uncatalyzed rate under these conditions was 1.35×10$^{-6}$ min$^{-1}$. The antibody was found to undergo at least 16 turnovers before a reduction in velocity was seen, due to inhibition of the reaction by the product p-nitrophenol (pnp). The $K_i$ for p-nitrophenol determined from a Dixon plot was 10.1±2.1 μM shown in FIG. 8b. The $K_i$ is defined as the negative x-coordinate of the intersection point of the lines in a Dixon plot.

Metal Dependence. Antibody 6A1A6 was dependent upon a metal ion cofactor. Addition of EDTA to reactions resulted in a linear loss of activity indicating a metal dependence. Subsequent addition of MgCl$_2$ restored catalysis with 10 mM required for optimal activity. The metal ions Ni$^{2+}$, Ca$^{2+}$, Mn$^{2+}$, and Co$^{2+}$ did not appear to increase the reaction rate; however, at the high pH required for this reaction it is likely that a concentration required for catalysis could not be achieved. Precipitates were often observed in reaction wells even at concentration as low as 0.5 mM.

Control Experiments. Several experiments provide evidence that the observed catalysis was due to the antibody. Catalytic activity is precipitated by addition of anti-mouse antibody. Antibody 6A1A6 was incubated with anti-mouse antibody and the antibody:anti-antibody complex was pelleted. No hydrolysis above background was seen in the supernatant. In addition, the reaction is inhibited by the addition of free hapten. Competitive inhibition indicates that the substrate and the hapten have the same binding site. This implies that the hapten was rationally designed for inducing an antibody binding site capable of catalysis on the substrate.

$F_{ab}$ fragments (purified on a Protein A column) retain 39±9% of the original activity. The $F_{ab}$ is a proteolytic fragment of the antibody that contains the antigen (substrate) binding domain. Retention of activity indicates that the antibody binding site is the catalytic site.

EXAMPLE IV

Hydrolysis of p-nitrophenyl Phosphate (pNPP)

Phosphomonoester Substrate. Under reaction condition identical to those used for pNPPT, the antibody also catalyzes the hydrolysis of p-nitrophenyl phosphate (pNPP). $K_{cat}$ and $K_m$ are 0.424±0.042 min$^{-1}$ and 357±54 μM, respectively. The uncatalyzed rate was 3.4×10$^{-6}$ min$^{-1}$.

The same control experiments were performed to show that hydrolysis was due to the antibody. Catalytic activity was precipitated by addition of anti-mouse antibody, the results are summarized in Table 7. The correlation between remaining antibody and activity indicates that catalysis was due to the antibody. In this case, the immunoprecipitation was quantitative with loss of catalytic activity. $F_{ab}$'s retain 47±5% of the activity of the original antibody. This reaction is similarly competitively inhibited by p-nitrophenyl (pnp) ($K_i$=9.31±1.94 μM) and hapten ($K_i$=199±54 μM).

TABLE 7

| Theoretical % Ig remaining | Calculated % Ig remaining | $V_i$ (mOD/min) | % relative activity |
| --- | --- | --- | --- |
| 100 | 100 | 0.120 | 100 |
| 82 | 98 | 0.107 | 89 |
| 64 | 91 | 0.101 | 84 |
| 54 | 61 | 0.076 | 63 |
| 28 | 25 | 0.035 | 28 |
| 0 | 0 | −0.025 | 0 |

While pNPPT and pNPP were substrates, antibody 6A1A6 demonstrated limited selectivity among phosphate esters with p-nitrophenyl leaving groups. Other p-nitrophenyl-containing molecules were tested and found not to be substrates. These include thymidine-3'-monophosphate-p-nitrophenyl ester (TpNPP), p-nitrophenyl phenyl phosphonate, a substrate for 5'-nucleotide phophodiesterases (those that are capable of hydrolysis of pNPPT, but not TpNPP), and the nonspecific phophodiesterase substrate bis (p-nitrophenyl) phosphate. It is possible that levels of pnp present in the substrate bis (p-nitrophenyl) were high enough to inhibit the catalytic activity.

EXAMPLE V

Hydrolysis of Adenosine Triphosphate

Adenosine triphosphate (ATP) contains phosphoanhydride bonds. Antibody 6A1A6 was capable of hydrolyzing all phosphate groups of ATP in a metal dependent fashion similar to that of p-nitrophenyl esters. ATP was useful for characterization of the antibody under conditions of neutral pH, rather than being constrained to the basic conditions required in the pnp system discussed in the above Examples.

Radiolabeled compounds were obtained from either Amersham: [8-$^{14}$C]ATP (catalog number CFA.330) and [$^{14}$C(U)]AMP (catalog number CFA.305); or NEN: [8-$^{14}$C]ADP (catalog number NEC-559, [γ-$^{32}$P]ATP (catalog number NEG-502A), [α$^{32}$P]ATP (catalog number NEG-003H), and tetrasodium pyrophosphate (catalog number NEX-019).

Thin Layer Chromatography. Reactions were quenched and analyzed by spotting on a TLC plate. Two systems were used. PEI-cellulose coated plates were run in 1.5 M formic acid/0.5 M LiCl ($R_f$ values: ATAP, 0.3; $P_i$, 0.8). (In some cases it was useful to pre-run the TLC plate in H$_2$O to reduce smearing). Silica coated plates were run in isopropanol:NH$_4$OH:H$_2$O, (50:25:25) ($R_f$ values: ATP, 0.36; ADP, 0.55; AMP, 0.7; and Adenosine, 0.95). Assays involving the visualization of pyrophosphate used two TLC systems simultaneously: the silica system described ($R_f$ values: PP$_i$,O; Pi, 0.3), and a PEI-cellulose system run in 0.3 M sodium phosphate, pH=7.0 ($R_f$ values: ATP, 0.2; ADP, 0.4; AMP, 0.6; PP$_i$, 0.15; and P$_i$, 0.65). Radioactivity was quantitated using a Molecular Dynamics PhosphorImager.

Metal dependence. Reactions were performed at 36° C. with 9 pmol antibody, 1 nmol [γ-$^{32}$P]ATP, and 0.5 mM EDTA in 40 mM HEPES, 150 mM NaCl, pH 7.6. Each metal was titrated between 0 and 40 mM (or to the solubility limit) and the reaction quenched at one or two hours and analyzed by the PEI-cellulose TLC system. The extent of hydrolysis of the γ-phosphate was measured.

pH Profile. Assays were carried out in duplicate at different pH's using various buffers. In each reaction the buffer concentration was 40 mM with 150 mM NaCl, 0.5 mM EDTA, and 1 mM MgCl$_2$. The pH's and buffers used were: 6, MES; 6.8 and 7.6, HEPES; 8.0, HEPES or TAPS; 8.5, TAPS or CHES; 9.0, CHES; 9.9 and 10.9, CAPS. In each assay, 9 pmol antibody and 1 nmol [γ-$^{32}$P]ATP were used. (Final concentrations were 0.45 μM Ig and 50 μM ATP.) The reaction was performed at 37° C. and quenched after one hour and analyzed by the PEI-cellulose TLC system. The extent of hydrolysis of the γ-phosphate was measured.

Kinetic Assays Using $^{14}$C-Labeled Compounds. Assays were performed with [8-$^{14}$C]ATP, [8-$^{14}$C]ADP, and [$^{14}$C(U)] AMP. ADP and AMP were supplied in a 50% ethanol solution, which was found to be inhibitory. Immediately before each reaction, the solution was evaporated to dryness in vacuo and the compound resuspended in an equal volume of water. Assays were performed in duplicate at 37° C. in 0.5 mM EDTA, 1 mM MgCl$_2$, 40 mM CHES, 150 Mm NaCl, pH 9.0 and 1.9 μM antibody. Reactions were quenched and analyzed by the silica TLC system.

Kinetic Assays Using $^{32}$P-Labeled Compounds. Tetrasodium pyrophosphate (final concentration, 50 μM) was assayed at 37° C. in 40 mM CHES pH=9.0, with 150 mM NaCl, 0.5 mM EDTA, and 1 mM MgCl$_2$ and 1.9 μM antibody. Conditions for [γ-$^{32}$P]ATP were identical to those for [8-$^{14}$C]ATP.

Metal Dependence. Several metal ions were tested for their ability to act as a cofactor for antibody 6A1A6. All metal ions were tested in a range from 0–40 mM. In general it was found that antibody catalytic activity correlated with increasing metal ion concentration up to about 1 mM in most cases. (This was not the case if the solubility limit of the metal ion was reached. Here the rate tended to level off.) At concentrations above this optimum, activity was reduced. The results of hydrolysis assays performed with different metal ions are shown below in Table 8. The antibody accepts a range of divalent metals as cofactors with only small changes in the rate ($\leq$2-fold). No catalysis was seen in the presence of the monovalent cation Li$^+$ or in Na$^+$ containing assay buffer.

TABLE 8

| Metal Ion | Rate (min$^{-1}$) | Optimum Concentration (mM) | Relative Rate |
|---|---|---|---|
| Li$^+$ | 0 | 1 | 0.00 |
| Co$^{2+}$ | 15.3 ± 0.12 | 1 | 0.48 |
| Zn$^{2+}$ | 17.5 ± 2.02 | 20† | 0.54 |
| Cu$^{2+}$ | 20.2* | 20† | 0.63 |
| Ni$^{2+}$ | 24.6 ± 0.38 | 1 | 0.77 |
| Mg$^{2+}$ | 26.5 ± 0.09 | 1 | 0.82 |
| Ca$^{2+}$ | 30.9 ± 0.29 | 2 | 0.96 |
| Mn$^{2+}$ | 32.1 ± 0.05 | 1 | 1.00 |

*One data set was lost, preventing error analysis
†These ions were added to achieve this concentration. A precipitate was observed following the completion of the reaction, indicating an actual concentration lower than this.

pH dependence of the reaction was characterized in the presence of 1 mM Mg$^{2+}$. Mg$^{2+}$ was chosen because it is soluble throughout the pH range tested. The rate of the reaction appears to be optimal at approximately pH 9. The rate is relatively insensitive to pH, however, about a 2-fold difference in rate is observed throughout the range.

Figure 9A:
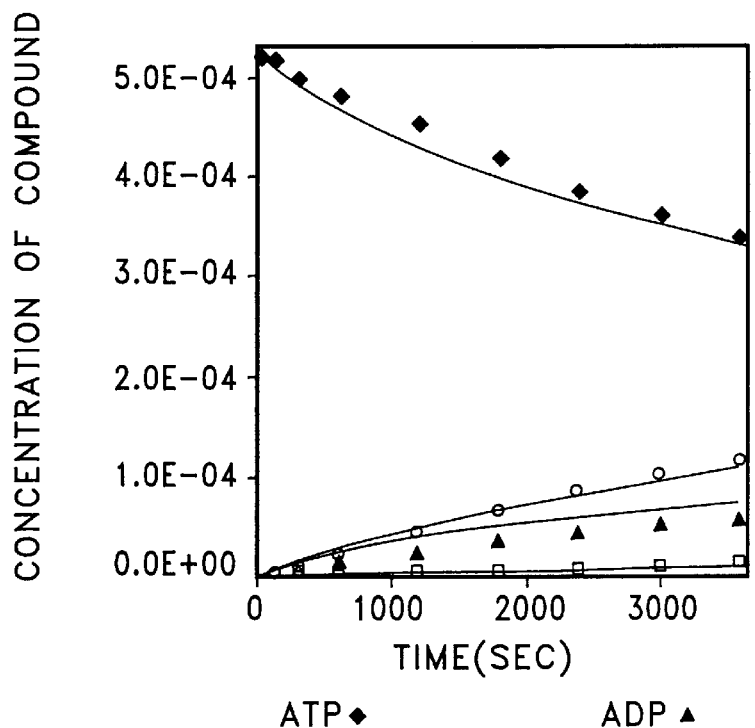
FIG. 9a is a graphical representation of the hydrolysis pattern of adenosine triphosphate (ATP) by monoclonal antibody 6A1A6.
Figure 9B:
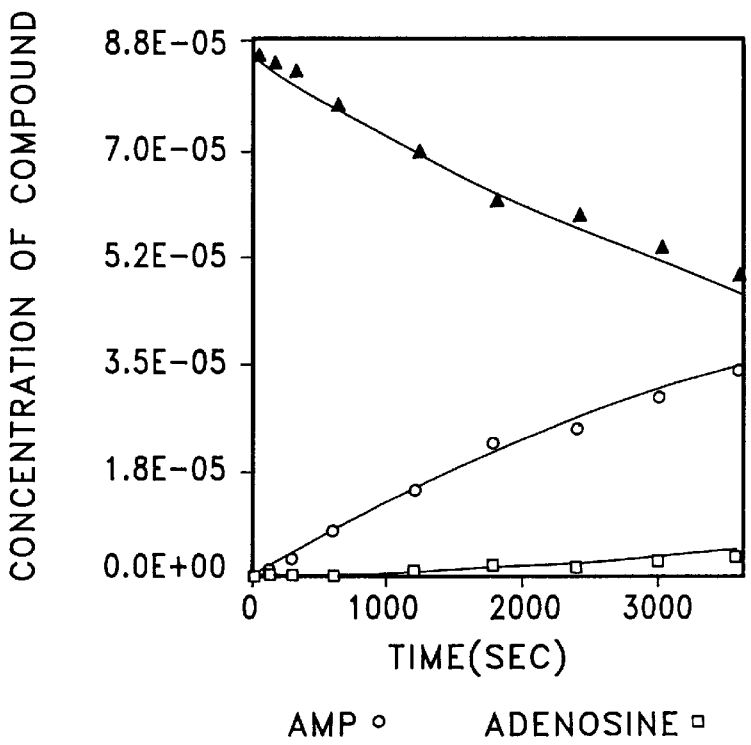
FIG. 9b is a graphical representation of the hydrolysis pattern of adenosine diphosphate (ADP) by monoclonal antibody 6A1A6.

Hydrolysis of ATP. As mentioned previously, all phosphate groups can be hydrolyzed from ATP by the antibody. The hydrolysis pattern of [8-$^{14}$C]ATP shown in FIG. 9a is not a typical precursor-product relationship that might be expected: the appearance of AMP is faster than the appearance of ADP. In addition, the final product adenosine appears very slowly. In order to explain this result, the kinetic behavior of ATP, ADP, and AMP was investigated. A summary of results is shown in Table 9.

TABLE 9

| Substrate | K$_m$ (μM) | V$_{max}$ (sec$^{-1}$) | V$_{max}$/K$_m$ |
|---|---|---|---|
| AMP | 161 ± 21 | 1.02 × 10$^2$ ± 0.03 × 10$^2$ | 6.32 × 10$^{-5}$ |
| ADP | 70 ± 8 | 1.20 × 10$^2$ ± 0.2 × 10$^2$ | 1.72 × 10$^{-4}$ |
| ATP | 1396 ± 123 | 9.5 × 10$^{-2}$ ± 1.3 × 10$^2$ | 6.83 × 10$^{-5}$ |

Evidence that the catalysis was due solely to the antibody was obtained using the standard control experiments described in the previous Examples. First, immunoprecipitation removed all catalytic activity. Second, F$_{ab}$ fragments were found to retain 36% of the original activity. Finally, the dithioate hapten was shown to be a competitive inhibitor of the reaction with a K$_i$ of 559 μM.

Reduction of activity at high metal ion concentrations is common in many enzyme systems. Most likely this indicates binding of the metal to a place other than the active site of the enzyme.

Many natural phosphoryl transfer enzymes that require magnesium for catalysis are able to utilize a number of divalent metals as cofactors. This is not true for the Ca$^{2+}$ dependent enzymes. One reason for this behavior may be that for Ca$^{2+}$, the metal is coordinated by amino acid residues at all coordination sites. Mg$^{2+}$ sites tend to have a solvent water coordinating and the size of the ion is not strictly regulated. Antibody 6A1A6 also has a wide tolerance for the size of metal ion cofactor.

The antibody is capable of producing two different products from ATP. This behavior is extremely unusual. Natural ATPases are very specific for cleavage of either the β- or γ-phosphate bond. This behavior could possibly be explained by noting that the K$_m$ for ATP is very high. Assuming that K$_m$=K$_D$, this weak binding indicates that it may be possible for the phosphates of ATP to move around in the active site until the β- or γ- phoshate is coordinated to a metal or an active site residue. The phosphate bound would determine the bond cleaved. Another plausible explanation is that the antibody recognizes the β-phosphate exclusively, and has no mechanism for influencing which side of the bond is cleaved.

EXAMPLE VI

Hydrolysis of Oligonucleotides by the Catalytic Antibodies of the Present Invention Antibody 6A1A6 was assayed for its ability to hydrolyze DNA. Oligomers 15 nucleotides in length were chosen for testing as they can be easily synthesized and purified. Synthesis And Purification. Oligomers were synthesized by standard protocols using either an AB1380A or 394 model DNA synthesizer. Oligomers were purified by denaturing polyacrylamide gel electrophoresis: 20% acrylamide (19:1 acrylamide/bis-acrylamide (w/w)), 7 M urea, 1× TBE. The oligomer band was visualized by UV shadowing and cut out with a razor blade. The band was crushed to a homogeneous slurry, four volumes of water added and the DNA eluted by shaking overnight at 25° C. or for two hours at 37° C. The eluted DNA was separated from the acrylamide slurry by centrifugation using a disposable chromatography column with a paper disc (Isolab product #QS-P). 1/10 Volume of 3M sodium acetate was added followed by three volumes of −20° C. ethanol. The solution was mixed thoroughly and incubated at −20° C. overnight. The solution was then centrifuged in Sorvall RC-5B Refrigerated Superspeed Centrifuge using an HB-4 swinging bucket rotor at 10,000 rpm (maximum 16,230 g) for 30 minutes. The supernatant was immediately decanted, the DNA pellet dried and resuspended in water. Concentration was determined using absorbance at 250 nm and a calculated ∈ value based on the oligomer sequence. Alternatively, oligomers were obtained from AmGen, Boulder, Inc.

5'-End Labeling. 5' end labeling of oligomers was performed using [γ-$^{32}$P]ATP (1.1 equivalents) and T4 polynucleotide kinase (10 units, New England Biolabs catalog number 201L) at 37° C. for 30 minutes in 50 mM Tris·HCl, 10 mM $MgCl_2$, 50 mM NaCl. Reactions were quenched at 90° C. for five minutes. Labeled oligomer was purified away from unincorporated label using gel filtration with Sephadex G-25. Typically, prepacked NAP columns from Pharmacia were used.

3'-End Labeling. This procedure was modified from that supplied with the terminal transferase enzyme (Boehringer Mannhiem catalog number 220582).

It was unknown what type of specificity antibody 6A1A6 would have for a DNA polymer. Several possible activities were monitored under conditions of pH 9 and 1 mM $Mg^{2+}$ that were optimal for ATP hydrolysis.

Endo- Vs. Exo- Nuclease. Type of nuclease activity was assessed from the pattern of hydrolysis products on gels. Oligomer 5'-$^{32}$P-$T_{15}$ showed a successive ladder of products. It appeared that the activity was exonucleolytic from the 3'-end. If activity was exonucleolytic from the 5'-end, the first cleavage product would have been radiolabelled thymidine 5'-monophosphate which then could be hydrolyzed to Pi and thymidine. These products were not observed on gels. At no time were shorter bands indicative of endonucleolytic activity detected.

5'-Phosphatase Activity. 5'-phosphatase activity was tested using oligomers that were 5'-$^{32}$p labelled with polynucleotide kinase and [γ-$^{32}$P]ATP. Gel electrophoresis of oligomers in an identical assay to that above indicated no release of $P_i$ as a product.

Kinetic Parameters. Kinetic experiments were performed with $T_{15}$ as a substrate. Due to the very slow rate of hydrolysis, experiments were done under single turnover conditions with enzyme excess. $K_m$ was determined to be 12±5 μM and $k_{cat}$ was found to be 0.0038±0.0018 $min^{-1}$.

Sequence Specificity. $T_{15}$ was chosen as the starting substrate because the original hapten contained a thymidine. A series of oligomers $T_{14}N$ (N=A, C, G, and T) were prepared and assayed for activity. The rates of cleavage were the same. A second series of oligomers $T_{13}NT$ (N=A, C, G, and T) were prepared and assayed. Again, no change in rate was seen. Another series of oligomers was tested: $T_{15}$, $A_{15}$, $C_{15}$, and $(G_3C)_3G_3$. $T_{15}$ and $C_{15}$ were found to be degraded at the same rate, while the rates of hydrolysis of $A_{15}$ and $(G_3C)_3G_3$ were found to be reduced.

Modified DNA. Oligomer $T_{14}$ containing phosphorothioate internucleotide linkages was assayed as a substrate. This analogue has one of the non-bridging oxygens of the internucleotide linkage replaced by sulfur. This oligomer was hydrolyzed by the antibody at the same rate as normal DNA. Recall that the original hapten 100 contained a phosphorodithioate linkage. Oligomer $T_{15}$ containing all dithioate linkages was assayed as a substrate. This oligomer was not hydrolyzed by the antibody.

Figure 10:
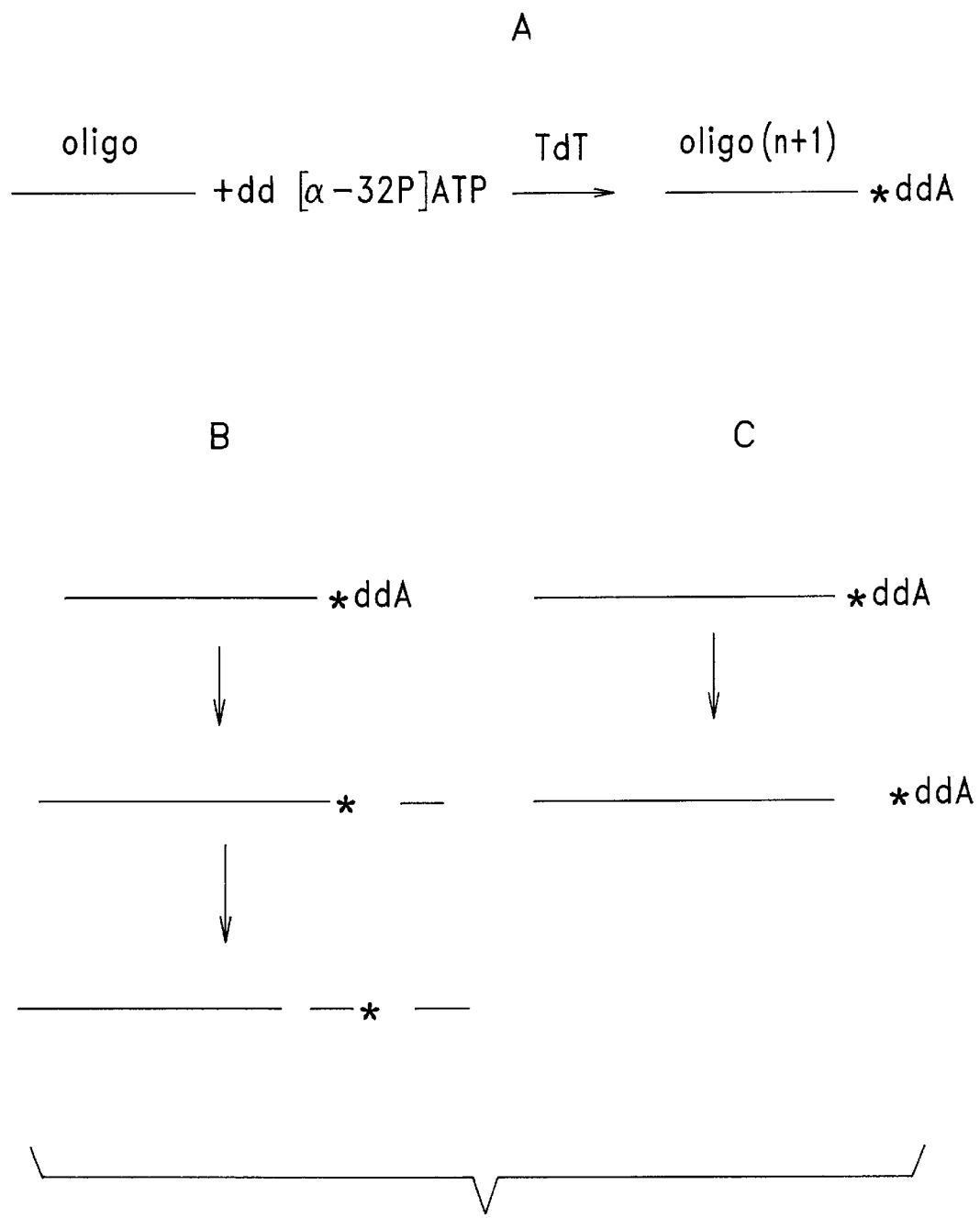
FIG. 10 is a schematic representation of the strategy for determining site of cleavage in the phosphodiester bond.

5' Vs. 3' Phosphodiesterase. The type of phosphodiesterase was determined using a 3'-end labelled oligomer in the strategy shown in FIG. 10. The distribution of products should indicate the hydrolysis site. Of concern was the presence of a dideoxynucleotide on the 3' end. It was unknown whether or not the antibody would recognize a dideoxy sugar. The results of these experiments were positive, yet somewhat surprising. The hydrolysis product seen on gels appeared to be a dimer as shown in FIG. 10, rather than a monomer as expected in 10c. Comparison with the marker compound 5'-$^{32}$P-TpA indicated that this product was 5'-pT-$^{32}$P-ddA. Thus, the antibody hydrolysis products have 5'-phosphates and 3'-hydroxyls.

Control Experiments. Standard controls were performed using oligomer $T_{15}$ as a substrate. Immunoprecipitation reduced activity by 93%. The remaining activity could be due to incomplete immunoprecipitation, but could also be due to a contaminating nuclease. The DNase activity is inhibited competitively by the hapten with a $K_i$ of 758±57 μM. $F_{ab}$ fragments retained 46±17% of the original activity.

EXAMPLE VII

Hydrolysis of Thymidine-3'-O-(7-Hydroxy-4-Methyl Coumarin) Phosphorodiester·$Et_3N$ A. Preparation of Thymidine-3'-O-(7-Hydroxy-4-Methyl Coumarin) Phosphorodiester·$Et_3N$.

(1) 5'-O-Dimethoxytritylthymidine-3'-O-[(β-Cyanoethyl) 7-Hydroxy-4-Methyl Coumarin] Phosphotriester. Coumarin (3.3 eq., 4.42 mmol, 0.780 g) and tetrazole solution (2.40 eq., 3.20 mmol, 2.25 mg, 7.15 mL) were added to 5'-O-Dimethoxytritylthymidine-3'-O-[(β-cynaoethyl)-N, N, diisopropyl]-phosphoramidite (1.00 g, 1.34 mmol) in dioxane (10 mL). After 1 hour $^{31}$P NMR exhibited two singlets (134.39, 133.87) which indicated that the reaction was complete. $I_2$ (10 mL of a 0.1 M solution in THF: $H_2O$: lutidine (2:2:1) (v/v)) was then added. The reaction was stirred for 12 hours at 4° C. A $^{31}$P NMR spectrum exhibited two singlets (7.91, 7.89) which indicated the oxidation was complete. The reaction was diluted in 50 mL EtOAc and extracted with 5% $Na_2SO_4$ (2×50 mL) and saturated NaCl solution (50 mL), and dried ($Na_2SO_4$). After evaporation of the solvent, the residue was dissolved in a minimal amount of EtOAc and precipitated into pentane. The resulting white/ yellow precipitate 5'-O-Dimethoxytritylthymidine-3'-O-[(β-Cyanoethyl)7-Hydroxy-4-Methyl Coumarin] Phosphotriester was coevaporated with $CH_3CN$. Yield: 900 mb, 1.08 mmol, 80.3%. $^{31}$P NMR: 7.91, 7.86.

(2) 5'-O-Dimethoxytritylthymidine-3'-O-7-Hydroxy-4-Methyl Coumarin Phosphodiester·$Et_3N$. 5'-O-Dimethoxytritylthymidine-3'-O-[(β-Cyanoethyl) 7-Hydroxy-4-Methyl Coumarin] Phosphotriester. (900 mg, 1.08 mmol) was dissolved in a minimal amount of $Et_3N$: $CH_3CN$ (1:1) and the reaction was stirred at 25° C. After 24 hours TLC showed the reaction was nearly complete ($R_f$: 0.1 ($CH_2Cl_2/CH_3OH$ (80:20))). The solvent was evaporated, and the residue dissolved in a minimal amount of $CH_2Cl_2$ and purified by flash chromatography and chomatographed as follows: first, side products were eluted using $Et_3N$/ EtOAc/$CH_3OH$ (65:10:10). Free coumarin ($R_f$: 0.2) was eluted with $CH_2Cl_2/CH_3OH$ (95:5). Finally, the product 5'-O-Dimethoxytritylthymidine-3 '-O-7-Hydroxy-4-Methyl Coumarin Phosphodiester·$Et_3N$ ($R_f$: 0.1) was eluted with $CH_2Cl_2/CH_3OH$ (80:20). Yield: 345 mg, 378 μmol, 35%. $^{31}$P NMR: 0.18.

(3) Thymidine-3'-O-(7-Hydroxy-4-Methyl Coumarin) Phosphodiester·$Et_3N$. 3% TCA in $CH_2Cl_2$ at 4° C. (10 mL) was added to 5'-O-Dimethoxytritylthymidine-3'-O-[(β-Cyanoethyl) 7-Hydroxy-4-Methyl Coumarin] Phosphodiester (345 mg, 378 μmol) cooled to 0° C. The reaction was allowed to proceed at 0° C. for 15 minutes. The reaction was quenched with pyridine/CH$_3$OH solution (1:1 (v/v)). The reaction mixture was concentrated and coevaporated once with toluene. The resulting gum was dissolved in a minimum of CH$_2$Cl$_2$ and applied to a preparative TLC plate (eluting solvent: CH$_2$Cl$_2$/CH$_3$OH/Et$_3$N (80:10:10)). The band corresponding to the product thymidine-3'-O-(7-Hydroxy-4-Methyl Coumarin) Phosphodiester·Et$_3$N (R$_f$: 0.15) was scraped off the TLC plate, crushed to a fine powder and eluted with CH$_3$OH. The CH$_3$OH was evaporated to recover thymidine-3'-O-(7-Hydroxy-4-Methyl Coumarin) Phosphodiester·Et$_3$N as a white solid. Yield: 117 mg, (171 μmol, 45%). Overall Yield: 12.8%. R$_f$: 0.15.

B. Hydrolysis of thynidine-3'-O-(7-Hydroxy-4-Methyl Coumarin) Phosphodiester·Et$_3$N.

Antibodies were assayed for their ability to cleave thymidine 3'-phosphate coumarin phosphodiester and methyl coumarin carbonate using an SLM 48000S fluorescence spectrometer at 25° C. Antibody concentrations were typically 0.5 μM. Metal ions, when used, were at 100 μM. The buffer system was 40 mM Tris·HCl or HEPES, 150 mM NaCl, pH=7.6. A fluorescence reading was recorded manually every 10 minutes for one hour. As an alternate assay, high performance liquid chromatography was used.

High performance liquid chromatography was performed using a Waters system consisting of chromatography pumps, a model 440 detector, and Maxima 820 software. The column was a Hamilton 5 μm Econosphere C$_{18}$, 150 mm×4.6 mm. The mobile phase was A: 100 mM NH$_4$OAc, B: Acetonitrile. B was increased from 0–25% over 25 minutes at a flow rate of 1 mL/min. After each elution, the column was washed with 100% B for 20 minutes, and reequilibrated with 100% A for 20 minutes. Retention times were as follows: thymidine 3'-coumarin phosphodiester, 26.9 min; thymidine 5'-coumarin phosphodiester, 27.3 min; thymidine 5'-phenyl phosphodiester, 26.3 min; thymidine, 15.4 min; thymidine 3'-phosphate, 4.3 min; thymidine 5'-phosphate, 3.2 min. This conclusion was based upon a fluorimetric assay taking advantage of the fluorescence of free coumarin.

Thymidine 3'-O-(7-hydroxy-4-methyl coumarin) phosphodiester (Thymidine 3'-coumarin) was assayed and found not to be a substrate for any of the monoclonal antibodies listed in Table 2.

EXAMPLE VIII

Hydrolysis of Methyl 7-Hydroxycoumarin Carbonate

A. Preparation of Methyl 7-Hydroxycoumarin Carbonate. Diisopropylethylamine (DIPEA) (1.1 eq., 5.5 mmol, 711 mg, 960 μL) was added to CH$_3$OCOCl (5 mmol, 472 mg, 425 μL) in DMF (15 mL). 7-hydroxy coumarin (5 mmol, 811 mg) in DMF (10 mL) was then added. After 1.5 hours the reaction was diluted in EtOAc (100 mL) and extracted with NaHCO$_3$ and saturated NaCl solutions. The product was recrystallized from CH$_3$OH resulting in light yellow crystals. Yield: 108 mg, 0.5 mmol, 10%.

B. Hydrolysis of Methyl 7-Hydroxycoumarin Carbonate. As the parent hapten is complementary to the transition state of a carbonate cleavage, the possibility existed that some antibodies would exhibit rate enhancements in the hydrolysis of carbonates. Methyl 7-hydroxycoumarin carbonate was examined as a possible substrate using the fluorimetric assay. While antibodies accelerated the hydrolysis of this substrate, the measured rate (data not shown) should be considered qualitative due to the numerous problems encountered using this assay.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

The embodiments of the invention in which an exclusive property or privilege is claimed are defined as follows:

1. A monoclonal antibody capable of hydrolyzing a substrate, said antibody having at least two binding sites, wherein the first binding site binds the substrate and the second binding site binds a free metal ion.

2. A monoclonal antibody of claim 1, wherein said antibody has esterolytic activity.

3. A monoclonal antibody of claim 1, wherein said antibody has phosphodiesterase activity.

4. A monoclonal antibody of claim 1, wherein said antibody is crossreactive with a plurality of metal ions.

5. A monoclonal antibody of claim 1, wherein said metal ion is a divalent cation.

6. A monoclonal antibody of claim 1, wherein said metal ion is a metallic cation selected from the group of metallic cations consisting of mercury, silver, cobalt, nickel, zinc, copper, cadmium, calcium, iron, manganese, and magnesium.

7. A monoclonal antibody of claim 1, wherein said metal ion is a metallic cation selected from the group of metallic cations consisting of mercury, silver, and cobalt.

8. A monoclonal antibody of claim 1, wherein said metal ion is nickel or zinc.

9. A method for producing a monoclonal antibody capable of hydrolyzing a substrate, comprising the steps of:
    (a) immunizing a host with an immunogenic mixture comprising a free metal ion and a hapten-carrier conjugate, wherein said hapten-carrier conjugate has an affinity for the free metal ion;
    (b) harvesting from said host, cells producing an antibody to said immunogenic mixture;
    (c) producing antibodies from said cells harvested from said host; and
    (d) identifying a monoclonal antibody capable of binding the substrate and the free metal ion.

10. A method for producing a monoclonal antibody according to claim 9, wherein said antibody has esterolytic activity.

11. A method for producing a monoclonal antibody according to claim 9, wherein said antibody has phosphodiesterase activity.

12. A method for producing a monoclonal antibody according to claim 9, wherein said antibody is crossreactive with a plurality of metal ions.

13. A method for producing a monoclonal antibody according to claim 9, wherein said free metal ion is a divalent cation.

14. A method for producing a monoclonal antibody according to claim 9, wherein said metal ion is a metallic cation selected from the group of metallic cations consisting of mercury, silver, cobalt, nickel, zinc, copper, cadmium, calcium, iron, manganese, and magnesium.

15. A method for producing a monoclonal antibody according to claim 9, wherein said metal ion is a metallic cation selected from the group of metallic cations consisting of mercury, silver, and cobalt.

16. A method for producing a monoclonal antibody according to claim 10, wherein said metal ion is nickel or zinc.

17. A method for producing a monoclonal antibody according to claim 9, wherein said hapten-carrier conjugate comprises a protein carrier, a linker covalently bonded to the carrier, and a chemical moiety covalently bonded to the linker, wherein said chemical moiety has an affinity for the metal ion.

18. A method for producing a monoclonal antibody according to claim 17, wherein said chemical moiety includes a stable derivative of a phosphodiester compound.

19. A method for producing a monoclonal antibody according to claim 18, wherein said stable derivative is selected from the group of phosphorus-containing moieties consisting of phosphorodithioate, phosphorothioate, methylphosphonate, and phosphoramidate.

20. A method for producing a monoclonal antibody according to claim 17, wherein said chemical moiety includes a sulfur derivative of a phosphodiester compound.

21. A method for producing a monoclonal antibody according to claim 20, wherein said sulfur derivative is phosphorodithioate.

22. A method for producing a monoclonal antibody according to claim 17, wherein said chemical moiety includes a nucleoside.

23. A method for producing a monoclonal antibody according to claim 22, wherein said nucleoside is thymidine.

24. A method for producing a monoclonal antibody according to claim 17, wherein said chemical moiety includes a fluorescent chromophore.

25. A method for producing a monoclonal antibody according to claim 24, wherein said fluorescent chromophore is a coumarin derivative.

26. A method for producing a monoclonal antibody according to claim 25, wherein said coumarin derivative is 7-hydroxy-4-methyl coumarin.

27. A method for producing a monoclonal antibody according to claim 17, wherein said chemical moiety includes a p-nitrophenyl ester leaving group.

28. A method for producing a monoclonal antibody according to claim 17, wherein said protein carrier is serum albumin or keyhole limpet hemocyanin.

29. A method for producing a monoclonal antibody according to claim 17, wherein said linker is a succinyl group.

30. A method for producing a monoclonal antibody according to claim 9, wherein the step of producing antibodies is accomplished using a hybridoma of myeloma immortal cells and mammalian immune cells sensitized against the immunogenic mixture.

31. A method for producing a monoclonal antibody according to claim 9, wherein the step of identifying antibodies is accomplished by an enzyme-linked immunosorbent assay.

32. A monoclonal antibody which is immunoreactive with a free metal ion and a hapten-carrier conjugate, said hapten-carrier conjugate having an affinity for the free metal ion, and wherein said hapten-carrier conjugate comprises a protein carrier, a linker covalently bonded to the carrier, and a chemical moiety covalently bonded to the linker, wherein said chemical moiety is a stable derivative of a phosphodiester compound.

33. A monoclonal antibody of claim 32, wherein said stable derivative is phosphorodithioate.

34. A hybridoma of myeloma immortal cells and mammalian immune cells from a mammal previously immunized with an immunogenic mixture, wherein;

the immunogenic mixture comprises a free metal ion and a hapten-carrier conjugate, wherein said hapten-carrier conjugate has an affinity for the free metal ion; and the hapten-carrier conjugate comprises a protein carrier, a linker covalently bonded to the carrier, and a chemical moiety covalently bonded to the linker, wherein said chemical moiety includes a stable derivative of a phosphodiester compound.

35. A hybridoma of claim 34, wherein the hybridoma produces a monoclonal antibody which is capable of hydrolyzing a substrate, said antibody having at least two binding sites, wherein the first binding site binds the substrate and the second binding site binds the metal ion.

36. A hybridoma of claim 34, wherein the hybridoma produces a monoclonal antibody having phosphodiesterase activity.

37. A hybridoma of claim 34, wherein said metal ion is a metallic cation selected from the group of metallic cations consisting of mercury, silver, cobalt, nickel, zinc, copper, cadmium, calcium, iron, manganese, and magnesium.

38. A hybridoma of claim 34, wherein the hybridoma produces a monoclonal antibody which immunoreacts with a nerve gas selected from the group of nerve gases consisting of tabun, sarin, and parathion.

* * * * *